US009447170B2

(12) United States Patent
Ko Ferrigno et al.

(10) Patent No.: US 9,447,170 B2
(45) Date of Patent: *Sep. 20, 2016

(54) MODIFIED STEFIN A SCAFFOLD PROTEINS

(71) Applicant: AVACTA LIFE SCIENCES LIMITED, Wetherby (GB)

(72) Inventors: Paul Ko Ferrigno, Leeds (GB); Elisenda Gendra, Leeds (GB)

(73) Assignee: Avacta Life Sciences Limited, Wetherby (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/478,910

(22) Filed: Sep. 5, 2014

(65) Prior Publication Data

US 2016/0024184 A1 Jan. 28, 2016

Related U.S. Application Data

(63) Continuation of application No. 12/988,106, filed as application No. PCT/GB2009/050380 on Apr. 16, 2009, now Pat. No. 8,853,131.

(30) Foreign Application Priority Data

Apr. 18, 2008 (GB) .................................. 0807065.8

(51) Int. Cl.
*C40B 40/10* (2006.01)
*C40B 30/04* (2006.01)
*A61K 38/00* (2006.01)
*C07K 14/81* (2006.01)

(52) U.S. Cl.
CPC ................................ *C07K 14/8139* (2013.01)

(58) Field of Classification Search
CPC .................................................. C07K 14/8139
USPC ........................ 506/18, 9; 530/324, 350, 300
See application file for complete search history.

(56) References Cited

U.S. PATENT DOCUMENTS

| | | | | |
|---|---|---|---|---|
| 8,063,019 | B2 | 11/2011 | Woodman et al. | |
| 8,853,131 | B2 * | 10/2014 | Ko Ferrigno | 506/9 |
| 2012/0190819 | A1 | 7/2012 | Woodman et al. | |

FOREIGN PATENT DOCUMENTS

WO WO-2006/131749 A2 12/2006

OTHER PUBLICATIONS

Davis et al. "Peptide Aptamers in Label-Free Protein Detection: 1. Characterization of the Immobilized Scaffold", *Anal. Chem.* 79:1089-1096 (2007).
Johnson et al. "Surface-Immobilized Peptide Aptamers as Probe Molecules for Protein Detection", *Anal. Chem.* 80:978-983 (2008).
Nikawa et al., "Studies on the reactive site of the cystatin superfamily using recombinant cystatin A mutants", *FEBS Letters* 255(2):309-314 (1989).
Pavlova et al. "The role of the second binding loop of the cysteine protease inhibitor, cystatin A (stefin A), in stabilizing complexes with target proteases is exerted predominantly by Leu73", *Eur. J. Biochem.* 269:5649-5658 (2002).
Shibuya et al. "Significance of the Highly Conserved Gly-4 Residue in Human Cystatin A", *J. Biochem.* vol. 118, pp. 635-642 (1995).
Woodman et al. "Design and Validation of a Neutral Protein Scaffold for the Presentation of Peptide Aptamers", *J. Mol. Biol.* 352:1118-1133 (2005).
International Search Report corresponding to International Application No. PCT/GB2009/050380 mailed Sep. 21, 2009.
Search Report corresponding to British Application No. GB0807065.8 dated Aug. 18, 2008.
PCT International Preliminary Report on Patentability, International Application No. PCT/GB2009/050380; Date of Mailing:Oct. 28, 2010.

* cited by examiner

*Primary Examiner* — Ganapathirama Raghu
(74) *Attorney, Agent, or Firm* — Myers Bigel & Sibley, P.A.

(57) ABSTRACT

The invention provides novel scaffold proteins for the display of peptides such as peptide aptamers. The novel scaffold proteins are modifications of Stefin A or STM (a variant of Stefin A) and are useful as scaffold proteins and as display systems.

14 Claims, 13 Drawing Sheets

A

B

C

D

SEQUENCE LISTING

```
<160> NUMBER OF SEQ ID NOS: 27

<210> SEQ ID NO 1
<211> LENGTH: 98
<212> TYPE: PRT
<213> ORGANISM: Homo sapiens

<400> SEQUENCE: 1

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Val
        35                  40                  45

Ala Gly Thr Asn Tyr Tyr Ile Lys Val Arg Ala Gly Asp Asn Lys Tyr
    50                  55                  60

Met His Leu Lys Val Phe Lys Ser Leu Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe


<210> SEQ ID NO 2
<211> LENGTH: 98
<212> TYPE: PRT
<213> ORGANISM: Homo sapiens

<400> SEQUENCE: 2

Met Ile Pro Trp Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Asp
        35                  40                  45

Ala Gly Thr Asn Tyr Tyr Ile Lys Val Arg Ala Gly Asp Asn Lys Tyr
    50                  55                  60

Met His Leu Lys Val Phe Asn Gly Pro Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe


<210> SEQ ID NO 3
<211> LENGTH: 9
<212> TYPE: PRT
<213> ORGANISM: Homo sapiens

<400> SEQUENCE: 3

Gln Val Val Ala Gly Thr Asn Tyr Tyr
1               5


<210> SEQ ID NO 4
<211> LENGTH: 9
```

<212> TYPE: PRT
<213> ORGANISM: Homo sapiens

<400> SEQUENCE: 4

Gln Val Asp Ala Gly Thr Asn Tyr Tyr
1 5

<210> SEQ ID NO 5
<211> LENGTH: 9
<212> TYPE: PRT
<213> ORGANISM: Homo sapiens

<400> SEQUENCE: 5

Gln Val Leu Ala Ser Thr Asn Tyr Tyr
1 5

<210> SEQ ID NO 6
<211> LENGTH: 18
<212> TYPE: PRT
<213> ORGANISM: Homo sapiens

<400> SEQUENCE: 6

Leu Lys Val Phe Lys Ser Leu Pro Gly Gln Asn Glu Asp Leu Val Leu
1 5 10 15

Thr Gly

<210> SEQ ID NO 7
<211> LENGTH: 18
<212> TYPE: PRT
<213> ORGANISM: Homo sapiens

<400> SEQUENCE: 7

Leu Lys Val Phe Asn Gly Pro Pro Gly Gln Asn Glu Asp Leu Val Leu
1 5 10 15

Thr Gly

<210> SEQ ID NO 8
<211> LENGTH: 18
<212> TYPE: PRT
<213> ORGANISM: Homo sapiens

<400> SEQUENCE: 8

Leu Lys Val Phe Asn Gly Pro Pro Gly Gln Asn Glu Asp Leu Val Arg
1 5 10 15

Ser Gly

<210> SEQ ID NO 9
<211> LENGTH: 98
<212> TYPE: PRT
<213> ORGANISM: Homo sapiens

<400> SEQUENCE: 9

Met Ile Pro Gly Gly Leu Ser Glu Ala Lys Pro Ala Thr Pro Glu Ile
1 5 10 15

Gln Glu Ile Val Asp Lys Val Lys Pro Gln Leu Glu Glu Lys Thr Asn
20 25 30

Glu Thr Tyr Gly Lys Leu Glu Ala Val Gln Tyr Lys Thr Gln Val Leu
35 40 45

Ala Ser Thr Asn Tyr Tyr Ile Lys Val Arg Ala Gly Asp Asn Lys Tyr
50 55 60

Met His Leu Lys Val Phe Asn Gly Pro Pro Gly Gln Asn Glu Asp Leu

-continued

```
65                  70                  75                  80

Val Arg Ser Gly Tyr Gln Val Asp Lys Asn Lys Asp Asp Glu Leu Thr
                85                  90                  95

Gly Phe


<210> SEQ ID NO 10
<211> LENGTH: 98
<212> TYPE: PRT
<213> ORGANISM: Homo sapiens

<400> SEQUENCE: 10

Met Ile Pro Arg Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Leu
        35                  40                  45

Ala Ser Thr Asn Tyr Tyr Ile Lys Val Arg Ala Gly Asp Asn Lys Tyr
    50                  55                  60

Met His Leu Lys Val Phe Asn Gly Pro Pro Gly Gln Asn Glu Asp Leu
65                  70                  75                  80

Val Arg Ser Gly Tyr Gln Val Asp Lys Asn Lys Asp Asp Glu Leu Thr
                85                  90                  95

Gly Phe


<210> SEQ ID NO 11
<211> LENGTH: 98
<212> TYPE: PRT
<213> ORGANISM: Homo sapiens

<400> SEQUENCE: 11

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Val
        35                  40                  45

Ala Gly Thr Asn Tyr Tyr Ile Lys Val Arg Ala Gly Asp Asn Lys Tyr
    50                  55                  60

Met His Leu Lys Val Phe Asn Gly Pro Pro Gly Gln Asn Glu Asp Leu
65                  70                  75                  80

Val Arg Ser Gly Tyr Gln Val Asp Lys Asn Lys Asp Asp Glu Leu Thr
                85                  90                  95

Gly Phe


<210> SEQ ID NO 12
<211> LENGTH: 98
<212> TYPE: PRT
<213> ORGANISM: Homo sapiens

<400> SEQUENCE: 12

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Leu
        35                  40                  45
```

```
Ala Ser Thr Asn Tyr Tyr Ile Lys Val Arg Ala Gly Asp Asn Lys Tyr
    50                  55                  60

Met His Leu Lys Val Phe Lys Ser Leu Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe


<210> SEQ ID NO 13
<211> LENGTH: 98
<212> TYPE: PRT
<213> ORGANISM: Homo sapiens

<400> SEQUENCE: 13

Met Ile Pro Arg Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Val
        35                  40                  45

Ala Gly Thr Asn Tyr Tyr Ile Lys Val Arg Ala Gly Asp Asn Lys Tyr
    50                  55                  60

Met His Leu Lys Val Phe Lys Ser Leu Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe


<210> SEQ ID NO 14
<211> LENGTH: 83
<212> TYPE: PRT
<213> ORGANISM: Homo sapiens

<400> SEQUENCE: 14

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Leu
        35                  40                  45

Ala Ser Thr Asn Tyr Tyr Ile Lys Val Arg Ala Gly Asp Asn Lys Tyr
    50                  55                  60

Met His Leu Lys Val Phe Asn Gly Pro Pro Gly Gln Asn Glu Asp Leu
65                  70                  75                  80

Val Arg Ser


<210> SEQ ID NO 15
<211> LENGTH: 73
<212> TYPE: PRT
<213> ORGANISM: Homo sapiens

<400> SEQUENCE: 15

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30
```

```
Glu Thr Tyr Gly Lys Leu Glu Ala Val Gln Tyr Lys Thr Gln Val Leu
        35                  40                  45

Ala Ser Thr Asn Tyr Tyr Ile Lys Val Arg Ala Gly Asp Asn Lys Tyr
    50                  55                  60

Met His Leu Lys Val Phe Asn Gly Pro
65                  70
```

<210> SEQ ID NO 16
<211> LENGTH: 83
<212> TYPE: PRT
<213> ORGANISM: Homo sapiens

<400> SEQUENCE: 16

```
Met Ile Pro Arg Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Leu
        35                  40                  45

Ala Ser Thr Asn Tyr Tyr Ile Lys Val Arg Ala Gly Asp Asn Lys Tyr
    50                  55                  60

Met His Leu Lys Val Phe Asn Gly Pro Pro Gly Gln Asn Glu Asp Leu
65                  70                  75                  80

Val Arg Ser
```

<210> SEQ ID NO 17
<211> LENGTH: 73
<212> TYPE: PRT
<213> ORGANISM: Homo sapiens

<400> SEQUENCE: 17

```
Met Ile Pro Arg Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Leu
        35                  40                  45

Ala Ser Thr Asn Tyr Tyr Ile Lys Val Arg Ala Gly Asp Asn Lys Tyr
    50                  55                  60

Met His Leu Lys Val Phe Asn Gly Pro
65                  70
```

<210> SEQ ID NO 18
<211> LENGTH: 83
<212> TYPE: PRT
<213> ORGANISM: Homo sapiens

<400> SEQUENCE: 18

```
Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Val
        35                  40                  45

Ala Gly Thr Asn Tyr Tyr Ile Lys Val Arg Ala Gly Asp Asn Lys Tyr
    50                  55                  60

Met His Leu Lys Val Phe Asn Gly Pro Pro Gly Gln Asn Glu Asp Leu
65                  70                  75                  80
```

-continued

Val Arg Ser

<210> SEQ ID NO 19
<211> LENGTH: 73
<212> TYPE: PRT
<213> ORGANISM: Homo sapiens

<400> SEQUENCE: 19

```
Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Val
        35                  40                  45

Ala Gly Thr Asn Tyr Tyr Ile Lys Val Arg Ala Gly Asp Asn Lys Tyr
    50                  55                  60

Met His Leu Lys Val Phe Asn Gly Pro
65                  70
```

<210> SEQ ID NO 20
<211> LENGTH: 83
<212> TYPE: PRT
<213> ORGANISM: Homo sapiens

<400> SEQUENCE: 20

```
Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Leu
        35                  40                  45

Ala Ser Thr Asn Tyr Tyr Ile Lys Val Arg Ala Gly Asp Asn Lys Tyr
    50                  55                  60

Met His Leu Lys Val Phe Lys Ser Leu Pro Gly Gln Asn Glu Asp Leu
65                  70                  75                  80

Val Leu Thr
```

<210> SEQ ID NO 21
<211> LENGTH: 73
<212> TYPE: PRT
<213> ORGANISM: Homo sapiens

<400> SEQUENCE: 21

```
Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Leu
        35                  40                  45

Ala Ser Thr Asn Tyr Tyr Ile Lys Val Arg Ala Gly Asp Asn Lys Tyr
    50                  55                  60

Met His Leu Lys Val Phe Lys Ser Leu
65                  70
```

<210> SEQ ID NO 22
<211> LENGTH: 83
<212> TYPE: PRT
<213> ORGANISM: Homo sapiens

<400> SEQUENCE: 22

Met Ile Pro Arg Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Val
        35                  40                  45

Ala Gly Thr Asn Tyr Tyr Ile Lys Val Arg Ala Gly Asp Asn Lys Tyr
    50                  55                  60

Met His Leu Lys Val Phe Lys Ser Leu Pro Gly Gln Asn Glu Asp Leu
65                  70                  75                  80

Val Leu Thr

<210> SEQ ID NO 23
<211> LENGTH: 73
<212> TYPE: PRT
<213> ORGANISM: Homo sapiens

<400> SEQUENCE: 23

Met Ile Pro Arg Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Val
        35                  40                  45

Ala Gly Thr Asn Tyr Tyr Ile Lys Val Arg Ala Gly Asp Asn Lys Tyr
    50                  55                  60

Met His Leu Lys Val Phe Lys Ser Leu
65                  70

<210> SEQ ID NO 24
<211> LENGTH: 98
<212> TYPE: PRT
<213> ORGANISM: Homo sapiens

<400> SEQUENCE: 24

Met Ile Pro Arg Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Leu
        35                  40                  45

Ala Ser Thr Asn Tyr Tyr Ile Lys Val Arg Ala Gly Asp Asn Lys Tyr
    50                  55                  60

Met His Leu Lys Val Phe Asn Gly Pro Pro Gly Gln Asn Ala Asp Arg
65                  70                  75                  80

Val Leu Thr Gly Tyr Gln Val Asp Lys Asn Lys Asp Asp Glu Leu Thr
                85                  90                  95

Gly Phe

<210> SEQ ID NO 25
<211> LENGTH: 100
<212> TYPE: PRT
<213> ORGANISM: Homo sapiens

<400> SEQUENCE: 25

-continued

```
Met Ile Pro Arg Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Leu
        35                  40                  45

Ala Leu Ala Ser Thr Asn Tyr Tyr Ile Lys Val Arg Ala Gly Asp Asn
    50                  55                  60

Lys Tyr Met His Leu Lys Val Phe Asn Gly Pro Pro Gly Gln Asn Ala
65                  70                  75                  80

Asp Arg Val Leu Thr Gly Tyr Gln Val Asp Lys Asn Lys Asp Asp Glu
                85                  90                  95

Leu Thr Gly Phe
            100


<210> SEQ ID NO 26
<211> LENGTH: 25
<212> TYPE: DNA
<213> ORGANISM: Artificial
<220> FEATURE:
<223> OTHER INFORMATION: Oligonucleotide primer

<400> SEQUENCE: 26

aggccttgat caccatggac tagca                                            25


<210> SEQ ID NO 27
<211> LENGTH: 46
<212> TYPE: DNA
<213> ORGANISM: Artificial
<220> FEATURE:
<223> OTHER INFORMATION: Oligonucleotide primer

<400> SEQUENCE: 27

aagtgctagc aggccttgat caccatggac tagcaagcac aaatta                     46
```

MODIFIED STEFIN A SCAFFOLD PROTEINS

RELATED APPLICATIONS

The present application is a continuation application of U.S. application Ser. No. 12/988,106, filed Oct. 15, 2010, now U.S. Pat. No. 8,853,131, which is a 35 U.S.C. §371 national phase application of PCT International Application No. PCT/GB2009/050380, having an international filing date of Apr. 16, 2009, claiming priority to Great Britain Patent Application No. 0807065.8, filed Apr. 18, 2008. The disclosures of each application are incorporated herein by reference in their entireties. The above PCT International Application was published in the English language as International Publication No. WO 2009/136182A1.

STATEMENT REGARDING ELECTRONIC FILING OF A SEQUENCE LISTING

A Sequence Listing in ASCII text format, submitted under 37 C.F.R. §1.821, entitled 1141-2TSCT_ST25.txt, 17,774 bytes in size, generated on Dec. 4, 2014 and filed via EFS-Web, is provided in lieu of a paper copy. This Sequence Listing is hereby incorporated by reference into the specification for its disclosures.

FIELD OF THE INVENTION

The present invention relates to novel scaffold proteins for the display of peptides, such as peptide aptamers. In particular, the invention relates to the use of modified Stefin A polypeptides and modified artificial proteins based on Stefin A, all for use as scaffold proteins and as display systems.

BACKGROUND

Study of protein interactions is vital to an understanding of many biological processes, such as the roles of gene products in vivo both in health and disease. Peptide aptamers in particular have emerged as important molecular tools that are useful for both basic and applied aspects of molecular medicine. Due to their ability to specifically bind to, and inactivate, a given target protein at the intracellular level, they provide an experimental strategy for functional protein analyses, both in vitro and in vivo. They may also be used against extracellular proteins. As well as applications in studying protein function, these tools may therefore be useful for molecular detection, diagnostics and/or as therapeutic agents. Peptides and peptide aptamers may be used free in solution. However, small peptides when unconstrained will tend to form structures which present a limited interaction surface. Furthermore, they will often lose conformational entropy upon association with target molecules, reducing free energy of binding and consequently free peptides will often not form tight non-covalent complexes, which is a problem. In addition, within cells peptides are rapidly degraded, which limits their effectiveness for the study of protein interactions in vivo, which is also a problem.

Rather than being used in free solutions, peptides of interest may be bound to physical supports, or displayed in the context of a larger polypeptide. The former cannot readily be applied to in vivo studies. In the latter, peptides are genetically inserted into the primary sequence of a simple, stable scaffold protein. The folding of the scaffold conformationally constrains the peptide, so peptide aptamers bind partners with high specificity and affinity. It is display in the context of a polypeptide which is important in the present invention. Such display is often brought about using scaffold proteins.

Prior art scaffolds have included inactivated staphylococcal nuclease, green fluorescent protein (GFP) and thioredoxin A (TrxA), as well as isolated protein folds such as the Z domain of staphylococcal protein A, "affibodies", anticalins, and ankyrin repeats. Further prior art scaffold proteins include the fibronectin type III domain ('Fn3'), lipocalin family proteins from which anticalins are derived, bilin binding protein (BBP), and others.

More recently (WO 2006/131749) describes several rational mutations made in Stefin A to improve it as a scaffold. The modified Stefin A scaffold comprises mutations at the following three sites Lys71-Leu73, V48D and G4W and is referred to as STM (Stefin A Triple Mutant). It was shown that the combination of these three mutations generated a protein that had minimal interactions with proteins in human cells, and in particular had lost all detectable interaction with its known natural partners. However, we found that insertion of peptides into the protein at position 71-73 led to a strong selection pressure for truncations of the protein at the end of the inserted peptide. Although such truncated proteins could display biological efficacy, this observation leads to concerns that a subset of peptides that are simply inserted at position 71-73 without truncation may not be freely available for interaction with a target protein, which is a problem. Furthermore, insertion of peptides at a single site inevitably limits the total surface area used for a protein interaction, which in turn limits binding affinity and potentially specificity.

The novel mutations made to Stefin A and to modified artificial proteins based on Stefin A such as STM (Stefin A Triple Mutant) as disclosed in the present invention provide alternative improved and more stable scaffold proteins and also provide display systems that are more versatile than those of the prior art. Moreover, these new protein scaffolds/display systems are also quite unpredictable as efficient and robust display entities. The new mutations described hereinafter have been made at specified diverse areas of the Stefin A/STM proteins and surprisingly have been found not to affect Stefin A/STM protein configuration or their potential function as scaffold proteins. Furthermore, with the improved scaffolds of the present invention by virtue of further engineering it is possible to provide modifications wherein the scaffolds have multiple insertions something that was not hitherto possible in the prior art scaffolds.

BRIEF SUMMARY OF THE DISCLOSURE

According to a first aspect of the invention there is provided a modified Stefin A polypeptide or modified STM protein wherein the modification comprises a single mutational change or a heterologous oligonucleotide encoding a peptide inserted at sites selected from the group comprising:

(i) a mutation at codon 4 wherein the Glycine of Stefin A or the Tryptophan of STM is replaced by another amino acid that is not Tryptophan for Stefin A or Glycine for STM or by a peptide encoded by the heterologous oligonucleotide; or (ii) any change or heterologous oligonucleotide encoding a peptide insertion in codons 46 to 54 inclusive, that encode amino acids comprising or constraining loop 1; or (iii) any change or heterologous oligonucleotide encoding a peptide insertion in codons 67 to 84 inclusive, that encode amino acids comprising or constraining loop 2.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Reference herein to a scaffold protein is to sequences fused together into one protein, the term is also synonymous with fusion protein. By a "fusion protein" is meant a protein that includes the scaffold protein of the invention joined to one or more different (i.e., "heterologous") peptides or proteins. The insertion of heterologous peptides or proteins enables the fusion protein to bind to a desired target.

The present invention is based upon the novel modifications including insertions of the wild type Stefin A protein itself, preferably the Stefin A is a human Stefin A, or to its triple mutant version, STM, rendering them into forms suitable for use as stable scaffold proteins whilst concomitantly advantageously rendering them biologically neutral by ablating biologically significant interactions and activities by mutation of residues that are required for natural interactions with either cathepsins or other unknown proteins. Furthermore, it is envisaged that the selected mutation or insertion site(s) are able to accept and constrain inserted peptides to produce for example peptide aptamers. Whereas studies in human may require a human scaffold, the use of for example mouse Stefin A, may be advantageous for studies of mouse model biology and/or disease, similarly Stefin A derived from other species or plants may also be of utility in that specific species. Accordingly, the scaffolds and presentation systems of the present invention are intended to be useful for any selected species and the derivation of the Stefin A is dependent on a user's requirements.

It will be appreciated that the changes in DNA sequences encoding the amino acid at codon 4 of either Stefin A or its STM form, or the changes in codons 46 to 54 inclusive, that encode amino acids comprising or constraining loop 1 of either Stefin A or its STM form, or the changes in codons 67 to 84 inclusive, that encode amino acids comprising or constraining loop 2 of either Stefin A or its STM form, can be independent of one another. That is to say the modifications to Stefin A protein may be at one of three different discrete areas or regions i.e. at position 4 or in constraining loop 1 or loop 2. Similarly, the modifications to the triple mutant form STM may also be at any one of the three specified independent discrete sites i.e. at position 4 or in constraining loop 1 or loop 2. The rest of the sequence of Stefin A or STM will be unaltered and comprise the sequences as set forth below.

The sequence of wild type human Stefin A is shown below as SEQ ID NO:1:

MIPGGLSEAKPATPEIQEIVDKVKPQLEEKTNETYGKLEAVQYKTQVVAG

TNYYIKVRAGDNKYMHLKVFKSLPGQNEDLVLTGYQVDKNKDDELTGF

The sequence of the triple mutant STM is shown below as SEQ ID NO:2, the mutation sites and thus where STM varies from wild-type Stefin A are marked in bold and underlined:

MIPWGLSEAKPATPEIQEIVDKVKPQLEEKTNETYGKLEAVQYKTQVDAG

TNYYIKVRAGDNKYMHLKVFNGPPGQNEDLVLTGYQVDKNKDDELTGF

Reference herein to a "mutational change" conveys that there is a permanent change in the genetic material the mutational change may be by addition(s) or deletions or insertion(s) or replacement(s) to the amino acid residue(s)

Preferably, in the embodiment where the single mutational change is Glycine at codon 4 of Stefin A, its replacement is selected from the group comprising G4V, G4I, G4L, G4M, G4F, G4P, G4N, G4V, G4Q, G4S, G4T, G4W, G4Y, G4R, G4H, G4K, G4D and G4E. More preferably the change is G4R, that is to say the Glycine is replaced by Arginine at codon 4.

Preferably, in the embodiment where the single mutational change is Tryptophan at codon 4 of STM, its replacement is selected from the group comprising W4V, W4I, W4L, W4M, W4F, W4P, W4N, W4V, W4Q, W4S, W4T, W4G, W4Y, W4R, W4H, W4K, W4D and W4E. More preferably the change is W4R, that is to say the Tryptophan is replaced by Arginine at position 4.

It has been found that a change in the 5' region of the Stefin A open reading frame encoding the amino terminal 8 amino acids of Stefin A or STM allows the introduction of a cleavage site for a restriction endonucelase or a targeted recombination site. For example, it is demonstrated herein that after changing the DNA sequence to encode for example an Arginine at position 4 (replacing the wild type Glycine, or the Tryptophan in STM) allows the production of a surprisingly stable protein that possess the same biophysical characteristics as STM, but where the open reading frame now possess a unique restriction site for an enzyme such as and without limitation the enzyme AvrII, and thus serves an alternative and efficient scaffold protein.

Preferably, in the embodiment where the mutational change is any change in codons 46 to 54 inclusive that encode amino acids comprising or constraining loop 1 of Stefin A (SEQ ID NO:3 QWAGTNYY) or STM (SEQ ID NO:4 QVDAGTNYY) the change comprises for example QVLASTNYY (SEQ ID NO:5). It has been surprisingly demonstrated that introducing a sequence of amino acids such as, and without limitation, Leucine, Alanine, Serine at positions 48, 49 and 50, leads to a protein with the same biophysical characteristics as STM, and is thus likely to be an efficient scaffold.

Preferably, the mutational change in Stefin A is at 48-VAG-50 and in STM is at 48-LAS-50 such that the result is 48-LXS-50, wherein X is any amino acid.

Preferably, in the embodiment where the mutational change is any change in codons 67 to 84 inclusive that encode amino acids comprising or constraining loop 2 of Stefin A (SEQ ID NO:6 LKVFKSLPGQNEDLVLTG) or STM (SEQ ID NO:7 LKVFNGPPGQNEDLVLTG) the change comprises for example SEQ ID NO:8 LKVFNGP-PGQNEDLVRSG. It has been surprisingly demonstrated that a sequence of amino acids such as Arginine followed by a Serine (to replace Leucine 82 and threonine 83 of Stefin A or STM) leads to the production of a stable protein that, like STM, may serve as a good scaffold for the presentation of peptide aptamers.

Preferably, the mutational change in Stefin A is at 71-KSL-73 and 82-LT-83 and in STM is at 71-NPG-73 and 82-LT-83 such that the result is 71-NxP-73 and 82-RS-83, wherein X is any amino acid.

Preferably, in a further embodiment of the invention there is a further mutational change in Stefin A and STM which is at 82-LT-83 such that the result is 82-XX-83, wherein X is any amino acid and in a particularly preferred embodiment it is 82-RS-83. The mutational change may be at either 82 or 83 or at both positions.

Preferably, the mutational change may be any combination of those herein before mentioned with for example and without limitation, 82-XX-83 and a particular preferred variant has mutational changes at least at positions 71-73 and/or 82-83.

In another aspect the invention relates to a modified Stefin A polypeptide or modified STM protein comprising two mutational changes or a heterologous oligonucleotide encoding a peptide insertions at sites selected from the group comprising:

(i) a mutation at codon 4 wherein the Glycine of Stefin A or the Tryptophan of STM is replaced by another amino acid that is not Tryptophan for Stefin A or Glycine for STM or by a peptide encoded by the heterologous oligonucleotide; and/or (ii) any change or heterologous oligonucleotide encoding a peptide insertion in codons 46 to 54 inclusive, that encode amino acids comprising or constraining loop 1; and/or (iii) any change or heterologous oligonucleotide encoding a peptide insertion in codons 67 to 84 inclusive, that encode amino acids comprising or constraining loop 2.

It will be appreciated that in this aspect of the invention, where the modified Stefin A may comprise two mutations, it may comprise for example a mutation at position 4 and a change in any of codons 46 to 54 having loop 1 function or it may comprise a mutation at position 4 and a change in any of codons 67 to 84 having loop 2 function or it may comprise a change in any of codons 46 to 54 having loop 1 function and change in any of codons 67 to 84 having loop 2 function.

Similarly, the STM may comprise a mutation at position 4 and a change in any of codons 46 to 54 having loop 1 function or it may comprise a mutation at position 4 and a change in any of codons 67 to 84 having loop 2 function or it may comprise a change in any of codons 46 to 54 having loop 1 function and change in any of codons 67 to 84 having loop 2 function or it may comprise a change in any of codons 67 to 84 having loop 2 function.

In a yet further aspect the invention which relates to a modified Stefin A polypeptide or modified STM protein wherein the modification mutational changes or a heterologous oligonucleotide encoding a peptide inserted at three sites:

(i) a mutation at codon 4 wherein the Glycine of Stefin A or the Tryptophan of STM is replaced by another amino acid that is not Tryptophan for Stefin A or Glycine for STM or by a peptide encoded by the heterologous oligonucleotide; and (ii) any change or heterologous oligonucleotide encoding a peptide insertion in codons 46 to 54 inclusive, that encode amino acids comprising or constraining loop 1; and (iii) any change or heterologous oligonucleotide encoding a peptide insertion in codons 67 to 84 inclusive, that encode amino acids comprising or constraining loop 2.

Thus in this particular embodiment of the invention the modified Stefin A and STM comprises all three mutational changes as hereinbefore described. Thus the modified Stefin A or STM scaffold proteins comprises three specific mutations at position 4 and a change in both loop 1 and 2.

In another aspect the invention relates to a modified Stefin A polypeptide or modified STM protein comprising any single or combination of the sequences listed above, but terminating at either residue 73 of Stefin A or STM, or residue 84 of Stefin A or STM, and either with or without the insertion of a new amino acid sequence at these positions. We have found that there is a strong selection pressure for a stop codon following insertion of amino acid sequences after the NGP of STM, but that surprisingly such truncated proteins are both stable and capable of interfering with the biological functions of a target protein.

The present invention therefore also includes truncated or shortened modified Stefin A and STM scaffold proteins ideally shortened by 15 or 25 residues at the C-terminus end and thus terminating at either residues 73 or 84 of either Stefin A or STM. Also included in the invention are truncated or shortened modified Stefin A or STM that are shortened by any integer between 15 and 25 and thus terminate a residues between 73 to 84 of Stefin A or STM.

The present invention preferably includes all of the variants described, as each one allows the introduction of a heterologous peptide at one or more sites of the Stefin A or STM variant, by insertion of an oligonucleotide into an engineered restriction site in the open reading frames we have created. Thus the present invention provides several new scaffolds based on:

A unique heterologous peptide inserted into the protein at position 4, with the rest of the protein resembling either Stefin A or STM or one of the other variants described herein.

A unique heterologous peptide inserted into the protein at position 46-54 and especially at positions 48/49/50, with the rest of the protein resembling either Stefin A or STM or one of the other variants described herein.

A unique heterologous peptide inserted into the protein at position 67-84 and especially at position 71/72/73 with the rest of the protein resembling either Stefin A or STM or one of the other variants described herein.

A unique heterologous peptide inserted into the protein at position 67-84 and especially at position 82/83 with the rest of the protein resembling either Stefin A or STM or one of the other variants described herein.

Any combination of multiple peptides inserted into positions 4 and/or 48/49/50 and/or 71/72/73 and/or 82/83.

Any combination of single or multiple peptides inserted into positions 4 and/or 48/49/50 and/or 71/72/73 and/or 82/83 that is followed by a stop codon that removes or replaces the last 25 or the last 15 amino acid residues of either Stefin A or STM.

A particular advantage of the scaffold proteins of the present invention and the new mutations is that they enable the use of the whole of loop 1 or loop 2, or both loop 1 and loop 2 as well as the amino terminus. Together, these mutations will allow the presentation of surfaces at least as large as those used by antibodies. In addition, each can be used singly, or they can be used pair-wise or in multiple combinations with other mutations. The differing positions of the interaction surfaces, combined with the differing interactions between peptides inserted at the different sites, is likely to provide novel uses of the scaffold, such as where peptides that could not be presented for useful interaction at one site may now be presented by another, or where combinations of peptides at different sites allow a given peptide to switch from a non-interacting to an interacting conformation. In addition, any of these new mutations may be used in the context of full length Stefin A, full length STM, the full length proteins disclosed herein, or in the mutant versions of any of these proteins where the last residue derived from either Stefin A or STM is Leu73 of SteA or its new variants described here, or Pro73 of STM or its new variants, or the last residue of an inserted heterologous peptide where the last 15 or 25 amino acids of Stefin A or STM have been truncated.

In another aspect the invention relates to isolated nucleic acids comprising nucleotide sequences encoding the amino acid sequences of a scaffold protein or polypeptides as hereinbefore described above.

In another aspect the invention it relates to a method for identifying a target peptide capable of binding a structure of interest comprising providing a modified stefin A or STM protein scaffold protein as herein before described comprising a target peptide; contacting said scaffold protein with said structure of interest; and monitoring the association between the scaffold and the structure of interest, wherein association of the scaffold protein with the structure of interest identifies the target peptide as a candidate target peptide capable of binding said structure.

In a further aspect of the invention the scaffold protein is selected from the group comprising:

```
SEQ ID NO: 9 (SDM):
MIPGGLSEAK PATPEIQEIV DKVKPQLEEK TNETYGKLEA

VQYKTQVLAS TNYYIKVRAG DNKYMHLKVF NGPPGQNEDL

VRSGYQVDKN KDDELTGF*

SEQ ID NO: 10 (SQM):
MIPRGLSEAK PATPEIQEIV DKVKPQLEEK TNETYGKLEA

VQYKTQVLAS TNYYIKVRAG DNKYMHLKVF NGPPGQNEDL

VRSGYQVDKN KDDELTGF*

SEQ ID NO: 11 (SUC):
MIPGGLSEAK PATPEIQEIV DKVKPQLEEK TNETYGKLEA

VQYKTQVVAG TNYYIKVRAG DNKYMHLKVF NGPPGQNEDL

VRSGYQVDKN KDDELTGF*

SEQ ID NO: 12 (SUM):
MIPGGLSEAK PATPEIQEIV DKVKPQLEEK TNETYGKLEA

VQYKTQVLAS TNYYIKVRAG DNKYMHLKVF KSLPGQNEDL

VLTGYQVDKN KDDELTGF*

SEQ ID NO: 13 (SUN):
MIPRGLSEAK PATPEIQEIV DKVKPQLEEK TNETYGKLEA

VQYKTQVVAG TNYYIKVRAG DNKYMHLKVF KSLPGQNEDL

VLTGYQVDKN KDDELTGF*

SEQ ID NO: 14 (SDM-):
MIPGGLSEAK PATPEIQEIV DKVKPQLEEK TNETYGKLEA

VQYKTQVLAS TNYYIKVRAG DNKYMHLKVF NGPPGQNEDL

VRS*
```

-continued

```
SEQ ID NO: 15 (SDM--):
MIPGGLSEAK PATPEIQEIV DKVKPQLEEK TNETYGKLEA

VQYKTQVLAS TNYYIKVRAG DNKYMHLKVF NGP*

SEQ ID NO: 16 (SQM-):
MIPRGLSEAK PATPEIQEIV DKVKPQLEEK TNETYGKLEA

VQYKTQVLAS TNYYIKVRAG DNKYMHLKVF NGPPGQNEDL

VRS*

SEQ ID NO: 17 (SQM--):
MIPRGLSEAK PATPEIQEIV DKVKPQLEEK TNETYGKLEA

VQYKTQVLAS TNYYIKVRAG DNKYMHLKVF NGP*

SEQ ID NO: 18 (SUC-):
MIPGGLSEAK PATPEIQEIV DKVKPQLEEK TNETYGKLEA

VQYKTQVVAG TNYYIKVRAG DNKYMHLKVF NGPPGQNEDL

VRS*

SEQ ID NO: 19 (SUC--):
MIPGGLSEAK PATPEIQEIV DKVKPQLEEK TNETYGKLEA

VQYKTQVVAG TNYYIKVRAG DNKYMHLKVF NGP*

SEQ ID NO: 20 (SUM-):
MIPGGLSEAK PATPEIQEIV DKVKPQLEEK TNETYGKLEA

VQYKTQVLAS TNYYIKVRAG DNKYMHLKVF KSLPGQNEDL

VLT*

SEQ ID NO: 21 (SUM--):
MIPGGLSEAK PATPEIQEIV DKVKPQLEEK TNETYGKLEA

VQYKTQVLAS TNYYIKVRAG DNKYMHLKVF KSL*

SEQ ID NO: 22 (SUN-):
MIPRGLSEAK PATPEIQEIV DKVKPQLEEK TNETYGKLEA

VQYKTQVVAG TNYYIKVRAG DNKYMHLKVF KSLPGQNEDL

VLT*

SEQ ID NO: 23 (SUN--):
MIPRGLSEAK PATPEIQEIV DKVKPQLEEK TNETYGKLEA

VQYKTQVVAG TNYYIKVRAG DNKYMHLKVF KSL*

SEQ ID NO: 24 (SQT):
MIPRGLSEAK PATPEIQEIV DKVKPQLEEK TNETYGKLEA

VQYKTQVLAS TNYYIKVRAG DNKYMHLKVF NGPPGQNADR

VLTGYQVDKN KDDELTGF*

SEQ ID NO: 25 (SQL):
MIPRGLSEAK PATPEIQEIV DKVKPQLEEK TNETYGKLEA

VQYKTQVLALAS TNYYIKVRAG DNKYMHLKVF NGPPGQNADR

VLTGYQVDKN KDDELTGF*
```

In a further aspect of the invention there is provided use of the scaffold proteins of present invention as an agent selected from the group comprising diagnostics, therapeutics, biomarkers, agents to bind to and specifically detect biomarkers, rationalized drug design templates, targets or reagents for drug discovery, antibody substitutes and research tools.

In a yet further aspect of the invention there is provided use of the scaffold proteins of present invention as a fusion protein.

Preferred features herein before described apply mutatis mutandis to all and each aspects of the invention.

Taken together the results described hereinafter and above demonstrate that, the scaffolds of the present invention are amenable to engineering in multiple locations, with each change alone or in combination being surprisingly well tolerated and that any destabilising effects of the mutations are apparently magnified by insertions in the amino terminus and in loop 2. These sites cannot therefore be used routinely, but surprisingly some inserts are tolerated which will allow us to use them to improve the binding affinity and specificity of peptide aptamers in for example the SQM-loop1. In addition, loop 1 appears able to present a range of peptides with very little problem. This is very surprising, as this is the shortest loop.

DETAILED DESCRIPTION OF THE INVENTION

A "deletion" refers to a change in an amino acid or nucleotide sequence due to the absence of one or more amino acid residues or nucleotides. The terms "insertion" or "addition" refer to changes in an amino acid or nucleotide sequence resulting in the addition of one or more amino acid residues or nucleotides, respectively, to a molecule or representation thereof, as compared to a reference sequence, for example, the sequence found in the naturally occurring molecule. A "substitution" refers to the replacement of one or more amino acids or nucleotides by different amino acids or nucleotides, respectively.

In order to improve upon Stefin A or STM as a scaffold, it is desirable to be able to insert heterologous peptides at alternative sites, and/or at multiple sites. To do this required altering the open reading frame that codes for either Stefin A or for STM, so as to introduce restriction endonuclease recognition sites into which oligonucleotides encoding heterologous peptides could be inserted. Alteration of the open reading frame almost inevitably leads to an alteration of the amino acid sequence that comprises the expressed protein. Given that proteins have evolved to an optimum combination of function and stability, the most likely (and most frequently observed) outcome of a change to the amino acid sequence of a protein is a loss of secondary structure and hence of stability. In the present invention the new scaffold proteins retained stability (See Examples and Figures).

In order to ascertain whether the alterations made at the DNA (open reading frame) level that also alter the amino acid sequence of the new Stefin A/STM variants lead to decreased stability of the protein, all of the variants described here were expressed in *E. coli* and circular dichroism was used to compare their secondary structure composition to that of Stefin A. All the proteins were found to be equally well expressed in *E coli*, typically to approximately 28 mg variant protein/ml of bacterial culture (FIG. 1). Proteins were purified to near-homogeneity by affinity-chromatography using Ni-agarose, and the purified preparations diluted to 0.3 mg protein/ml. Each resulting sample was subjected to analysis by circular dichroism. This involves scanning the protein across a range of near-UV wavelengths, such that the ellipticity of the light is affected by secondary structure elements (alpha-helix or beta-strands) of the protein. The greater the proportion of secondary structure, the greater is the effect on the ellipticity. Because the effect is affected by protein concentration, proteins were diluted to 0.3 mg/ml immediately before the analysis. Because the effect is proportional to the number of peptide bonds in the protein being analysed, the molar ellipticity is shown, which takes this effect into account. The data are shown in FIG. 3. This data shows that the proportion of secondary structure is preserved between STM and the new variants, and that the presence of inserts in STM does not adversely affect its structure. Two variants (SUN and SQM) were noted that appeared to show increased structure compared to the others. This may be attributable to the acquisition of secondary structure in the amino terminal tail that is present in all these proteins, and would be driven by the replacement of Glycine (Stefin A) or Tryptophan (STM) at position 4 by Arginine, as this is the only change that is common to SUN and SQM, and these are the only variants to possess this alteration.

Scaffold

As is well known in the art, the term 'scaffold' refers to a protein which can present target peptides to solvent without its own structure being deformed by the target peptide. Regarding the presentation of peptide to solvent, this can be tested using immunoprecipitation experiments. For example, an indication that a peptide is being presented to solvent may be obtained by its availability to an antibody capable of recognising it. Thus, in order to test the ability of a scaffold protein to present a peptide to solvent, the scaffold comprising the peptide would be expressed and an antibody recognising the peptide would be used to try to immunoprecipitate the scaffold-peptide fusion. If this protein can be immunoprecipitated or captured on the antibody, this shows that the peptide was presented to solvent as is required by a scaffold protein. Another, or an alternative, indication that a peptide is being presented to solvent may be obtained by phosphorylation studies. By incorporating a phosphate acceptor site into the target peptide, and then contacting the scaffold-peptide fusion with the cognate kinase in conditions permissive of phosphorylation, then the presentation of the peptide to solvent can be verified. Phosphorylation of the peptide indicates correct presentation to solvent.

Concerning a scaffold protein's resistance to being deformed by the target peptide which it bears, this can be tested using techniques such as circular dichroism or thermal stability. Specifically, a circular dichroism analysis of a scaffold protein without target peptide inserted into it should be substantially the same as the circular dichroism characteristics of the same scaffold protein when bearing a target peptide. This provides a demonstration that the presence of the target peptide in the scaffold protein has not compromised or deformed the structure of the scaffold protein bearing it. Another way to test this resistance to deformation by the target peptide is by studying the thermal stability of the scaffold protein with and without target peptide inserted.

A scaffold protein must be able to accept a peptide insert. Preferably the peptide insert is 36 amino acids or less, preferably 20 amino acids or less. Preferably the target peptide insert is 12 amino acids or less.

A scaffold protein must be of known structure. By 'known structure' it is meant that the crystal structure or a solution structure (NMR structure) must be known.

Preferred Features of Scaffold Proteins According to the Present Invention

Preferably a scaffold protein constrains the target peptide. The presence of a constraint effect in a scaffold protein can be demonstrated by comparing the affinity of an entity binding the target peptide when the target peptide is in the scaffold protein with the affinity when the peptide is not in the scaffold protein. A difference in these two affinities indicates that the scaffold protein is constraining the peptide to assume a particular three dimensional conformation. Preferably a scaffold protein constrains a peptide so that it demonstrates an increased binding affinity when present in the context of the scaffold protein. In other words, preferably the scaffold protein decreases the entropic cost of binding and so increases the measured affinity when compared with binding of a free peptide.

In some embodiments, constraint may be provided by a single N-terminal or C-terminal fusion to the target peptide.

Preferably a scaffold protein provides the target peptide with an increased stability in vivo. This effect may be demonstrated by comparison of expression of the target peptide in the context of the scaffold protein with expression of the target peptide on its own. Preferably, the target peptide shows increased stability in the context of the scaffold protein.

A scaffold protein is preferably biologically neutral. By 'biologically neutral' it is meant that interactions with other known proteins have been abolished. Furthermore, any signalling abilities possessed by the protein are preferably removed. Thus, a preferred scaffold protein according to the present invention is the STM scaffold protein.

Biological neutrality is an advantage of the present invention since it does not exist in the majority of prior art scaffold proteins. For example, Thioredoxin A acts as a dominant negative of the natural redox pathways in cells. Furthermore, it is known to inhibit P53 and is known to inhibit BCL6 signalling pathways. Advantageously, the scaffold proteins of the present invention do not interfere with naturally occurring signalling pathways.

A scaffold protein should be small. By 'small' is meant less than 25 kDa, preferably less than 13 kDa. Most preferably a scaffold protein should be less than 110 aa (excluding target peptide insert).

Preferably a scaffold protein according to the present invention will be conformationally stable. By 'conformationally stable' it is meant that no conformational changes should take place. Preferably a scaffold protein has no hinge region. Preferably a scaffold protein has no PH domain. Preferably a scaffold protein has no SH3 domain. Preferably a scaffold protein has no SH2 domain. Preferably a scaffold protein has no 'WW domain. Preferably a scaffold protein has no 'WD' domain. Preferably a scaffold protein has no HEAT repeats. Preferably a scaffold protein has no Proline rich domain. Preferably a scaffold protein has no post-translational modification in cells. Preferably a scaffold protein has no other domain known to facilitate conformational changes.

A scaffold protein according to the present invention preferably has no protein-protein interaction domains. A protein will be considered to have no protein-protein interaction domains if these have been mutated so as to render them non-functional.

Preferably a scaffold protein according to the present invention has no post translational modifications. Thus, preferably a scaffold protein according to the present invention has no glycosylation site. This is an advantage over prior art scaffold proteins such as dystrophin because post translational modifications can interfere with interactions or create spurious interactions themselves.

As noted above, scaffold proteins should not be deformed by the peptide insert. On this criterion, green fluorescent protein would not be considered a scaffold protein because at least one third of inserted target peptides abolish the fluorescence of green fluorescent protein. This is a demonstration that the target peptide insert is deforming the structure of the protein. Therefore, it is not a scaffold protein according to the present invention since a scaffold protein should preferably not be deformed by the target peptide insert.

Thioredoxin A (TrxA) is a prior art scaffold protein. TrxA is small and is stable. However, the insertion of target peptides into TrxA takes place between two cysteine residues. Scaffold proteins according to the present invention advantageously avoid this arrangement because the cysteine residues in TrxA can undergo reversible disulphide bonding which can alter the conformation of the scaffold protein and can affect the conformation of the presented target peptide. Thus, preferably the insertion site for target peptide is not between two cysteine residues on the scaffold protein.

Design Considerations

Scaffold proteins preferably have one or more of the following features:

1) be of known structure, thereby allowing an informed choice of the site for peptide insertion or replacement;

2) be stable enough to constrain the folding of a broad range of peptides;

3) be biologically neutral, i.e. lack interactions with cellular proteins that could contribute a phenotype; and 4) be able to fold similarly, preferably identically in both prokaryotic and eukaryotic environments, so that data obtained in one system can inform experiments performed in the other.

The present invention provides a scaffold suited to the requirements of peptide aptamer technology. The scaffold proteins of the present invention preferably possesses all of the criteria defined above: the structure of parental Stefin A is known; the engineered scaffold is stable and tolerates the insertion of at least one peptide without losing its biophysical stability; it is able to present a broad range of peptides for functional interaction; and not only have all known biological interactions been engineered away.

Further Applications

It will be appreciated by the skilled reader that the use of peptide aptamers in microarrays is particularly advantageous when those peptide aptamers are presented in the scaffold protein according to the present invention. Prior art microarray technology relies heavily on antibodies. However, antibodies can lose specificity when they are bound to the array. Furthermore, recombinant proteins used in microarrays can provide information that proteins are present, but cannot provide information about what is binding them. By contrast, using peptide aptamers displayed in scaffold proteins according to the present invention can advantageously provide a lot more information when an array is interrogated. For example, upon observation of a binding partner, contextual information is advantageously derived when using a scaffold protein to display the aptamer. This advantage is characterised as the difference between a naïve and an informed library. Thus, in another aspect the invention relates to the use of these new scaffold proteins to display peptides on microarrays.

Preferably the scaffold protein according to the present invention is based on the sequence of Stefin A. By 'based on the sequence of Stefin A' it is meant that the scaffold protein should possess at least 30 of the 98 amino acid residues of Stefin A, preferably 25% of the amino acid sequence of Stefin A, preferably 30%, 40%, 50%, 60% or 70% of the amino acid sequence of Stefin A, preferably 80%, preferably 85%, preferably 90%, preferably 95% or even more of the sequence of Stefin A. Most preferably the scaffold protein will have the sequence of Stefin A or STM or one of the new variants disclosed herein and comprises one or more of the mutational changes hereinbefore described.

The ability of peptide aptamers to disrupt protein-protein interactions in vivo may allow the rapid identification of novel drug leads. Furthermore, the use of small, candidate drug molecule(s) to disrupt protein-protein interaction is advantageously facilitated by the present invention.

Use of peptide inserts comprising post-translational modification sites such as phosphorylation site(s) may be advantageously employed. This is beneficial in dissecting interactions which are varied according to the phosphorylation state of the target peptide. Furthermore, it allows the identification of candidate peptide aptamers which bind in a phosphorylation dependent manner.

In some embodiments, it may be desired to introduce disulphide bonds either side of the target peptide insert, for example by engineering a cysteine residue each side of the target peptide insert. This may be useful if the scaffold is being used exclusively in one setting. In this regard, it is to be noted that the family II cystatins use a di-sulphide bond to form elements of secondary structure that correspond to one preferred region of insertion. In the context of the present invention this can be achieved for example by the addition of a single cysteine at the C-terminus of the scaffold polypeptide, or within the target peptide such as at the C-terminal end of the target peptide, and addition of a second cysteine residue inserted at a second location such as in the N-terminus of the scaffold or at the N-terminal end of the target peptide, thus allowing cross-linking between the two. However, it is preferred to avoid the covalent constraint of peptides in this manner. Thus, in preferred scaffolds of the present invention, preferably the target peptide is not flanked by cysteine residues.

Overall it will be appreciated that different scaffolds may force a bias on the peptides they present, so that study of target peptides may advantageously involve peptides and/or libraries presented in more than one scaffold, so as to maximize the likelihood of success.

Scaffolds of the invention allow investigators to extend in vitro observations to the intracellular environment and vice versa, as well as allowing the in vitro identification or creation of tools that may be used inside cells without concerns about folding patterns or the oxidation state of disulphide bonds.

Peptide aptamers based on scaffolds of the present invention are tools that can be used to validate drug targets that can be used as components of diagnostic or prognostic tests or even form the basis for lead compounds for the treatment of human disease. The scaffolds of the invention, advantageously based on a full-length human protein, may be useful as biological therapeutics and/or in gene therapy.

Target Peptide

The term ‘target peptide’ as used herein refers to a peptide of interest. The target peptide is preferably a heterologous peptide. By heterologous is meant a peptide which is removed from its usual context, preferably a peptide having a sequence not usually found in the sequence of the scaffold protein bearing, carrying or displaying it. If the peptide does have a sequence which occurs elsewhere in the sequence of the scaffold protein, then for it to be ‘heterologous’ that sequence will be out of context i.e. not occupying its naturally occurring position (address) within the scaffold protein polypeptide. In this context, ‘position’ and means position within the linear amino acid chain rather than position in three dimensional space relative to other amino acid residues. The target peptide may be artificial for example generated by the construction of a library of peptides for incorporation into the scaffold protein. In these embodiments, the artificial peptide(s) are considered to be ‘heterologous’ for the purposes of the invention.

Peptide aptamers are peptides constrained and presented by a scaffold protein that are used to study protein function in cells. Some are able to disrupt protein-protein interactions and some are able to constitute recognition modules that allow the creation of a molecular toolkit for the intracellular analysis of protein function.

The ability to design or identify small molecules that can bind specifically and with high affinity to a given protein is a rate-limiting step in many experiments, including the development of protein microarrays, the analysis of proteins in the context of living cells and the validation of candidate drug targets. In nature, protein-protein interactions can be mediated by small surfaces of folded proteins. This has led to the use of small peptide surfaces presented within the context of a stable protein, called the scaffold, as protein recognition modules. Such reagents, called here peptide aptamers, have been used to disrupt biological protein activity in a range of systems.

Peptide aptamers are more easily delivered and more stable in cells than free peptides and their constrained folding results in a lower entropic cost of binding and hence increased affinity for target proteins. Protein engineering of peptide aptamers allows them to provide the recognition functionality in the design of a molecular toolkit although this potential has yet to be fully realized. The affinity of peptide aptamers for their targets ranges from $10''^{6}$ to $5\times10''^{9}$ M compared to IQ $10'^{7}$ to $10''^{11}$ M for antibody/target interactions. By using multiple insertions to increase the surface area of interaction, peptide aptamers are expected to be able to match or possibly advantageously exceed the binding affinities of antibodies. Nonetheless, peptide aptamers are clearly able to disrupt protein-protein interactions in vivo. Peptide aptamer screens are performed in yeast or in mammalian cells, which distinguishes them from phage display screens of peptide or antibody libraries performed against potentially misfolded prokaryotically expressed protein.

While the most extensively used scaffold is the *Escherichia coli* protein thioredoxin (TrxA), a number of other proteins have been used. The success of this technology hinges upon the robustness of the scaffold, yet one third of peptides may destabilize GFP, while many TrxA based peptide aptamers are not stably expressed in cultured human cells, suggesting that this scaffold also may not be rigid enough to present peptides without becoming itself partially unfolded. Peptides taken out of the context of one scaffold and placed in another frequently lose the ability to interact with their target proteins, raising the possibility that screens for constrained interactors with a given target may fail unless an appropriate scaffold is used. Finally, the biological activities of scaffolds used to present peptides have not been rigorously characterized in the prior art, leading to concerns that any phenotype observed when a peptide aptamer is expressed could, at least in part, be due to an effect of the scaffold and not the inserted peptide. We have therefore produced a robust, versatile, biologically neutral scaffold for the presentation of constrained peptides. We sought a protein that could be stably expressed in a range of experimental systems while presenting peptides that are able to interact functionally with a wide range of targets. Such a scaffold substantially improves peptide aptamer technology by increasing its robustness. In addition, by expanding the repertoire of available scaffolds, the present invention advantageously increases the likelihood that hits will be obtained in screens against a greater number of target proteins by using libraries in multiple scaffolds in simultaneous screens against each target.

Stefin A

Stefin A is the founder member of the cystatin family of protein inhibitors of cysteine cathepsins, which are lysosomal peptidases of the papain family. The stefin sub-group of the cystatin family is relatively small (around 100 amino acids) single domain proteins. They receive no known post-translational modification, and lack disulphide bonds, suggesting that they will be able to fold identically in a wide range of extra- and intracellular environments. SteA itself is a monomeric, single chain, single domain protein of 98 amino acids. The structure of SteA has been solved, facilitating the rational mutation of SteA into the STM scaffold. The only known biological activity of cystatins is the inhibition of cathepsin activity, which allowed us to exhaustively test for residual biological activity of our engineered proteins. Thus, we disclose that protein engineering of native SteA can produce variants that are useful as peptide aptamer scaffolds. The peptide aptamer prior art has been hampered by difficulties in identifying biological activity in cell-based assays, caused at least in part by sub-optimal performance of the various existing scaffolds. The present invention provides a useful scaffold that will be of great benefit to those seeking to study protein-protein interactions in vitro and in vivo.

Stefin A Sequences

A scaffold 'based on' stefin A has a sequence which is derived from stefin A. Preferably the sequence derived from stefin A comprises the stefin A wild type sequence, preferably comprising one or more of the modifications (mutations) described herein. It will be apparent to a person skilled in the art that minor modifications may be made to the scaffold sequence without departing from the invention. In particular, the invention relates to amino acid sequences and/or nucleotide sequences which have at least 25%, 35%, 45%, 55% or 60% identity to the corresponding sequences shown herein, preferably at least 70%, preferably at least 80%, preferably at least 85%, preferably at least 90%, preferably at least 92%, preferably at least 94%, preferably at least 95%, preferably at least 96%, preferably at least 97%, preferably at least 98%, preferably at least 99% identity, or even more, however in each case, sequence variations are considered 'minor' if they do not adversely affect the ability of the scaffold to present the target peptide to solvent, and do not restore or generate biological functions such as those which are possessed by wild type stefin A but which are abolished in mutational changes of the present invention.

Furthermore, minor modifications may also include small deletions or additions to the stefin A or stefin A derived sequences disclosed herein, such as addition or deletion of 10 amino acids or fewer to the stefin A derived polypeptide. Thus the invention relates to amino acid sequences having a total addition or deletion with respect to the stefin A or STM sequences disclosed herein of 40 amino acids or fewer, preferably 30 amino acids or fewer, preferably 20 amino acids or fewer, preferably 15 amino acids or fewer, more preferably 10 amino acids or fewer, preferably 9 amino acids or fewer, preferably 8 amino acids or fewer, preferably 7 amino acids or fewer, preferably 6 amino acids or fewer, preferably 5 amino acids or fewer, preferably 4 amino acids or fewer, preferably 3 amino acids or fewer, preferably 2 amino acids or fewer, preferably 1 amino acid. The total addition or deletion is the important factor, so that a difference of 9 or fewer may mean a deletion of 9 amino acids, or three deletions each of three amino acids, two additions of three amino acids and one deletion of three amino acids and so on. The invention also relates to the corresponding nucleic acid variants. In each case, sequence variations are considered 'minor' modifications if they do not adversely affect the ability of the scaffold to present the target peptide to solvent, and do not restore or generate biological functions such as those which are possessed by wild type stefin A.

Stefin A and STM Mutations

In the context of discussing mutation sites, 'close to' means within 7 amino acids, preferably within 5 amino acids, preferably within 3 amino acids, preferably within 2 amino acids, preferably at the nominated amino acid or one of the two neighboring amino acids.

In the context of insertions, it is preferred that at the nucleic acid level restriction site(s), preferably unique restriction site(s), are introduced to facilitate future insertions. These teachings and common general knowledge in the art of recombinant nucleic acid technology enable the skilled worker to introduce the relevant restriction site(s) whilst preserving the key features of the scaffold. By 'unique' is meant unique in the coding sequence of the scaffold protein. Non-unique sites may be used, but unique sites are preferred for ease of insertion and manipulation of the constructs. Where two or more sites are used for example to facilitate removal and replacement of the sequence of any of codons 67-84 of loop 1 of SteA, preferably each of the two or more sites is unique. However, if the two or more sites are identical it may advantageously simplify the removal and replacement operations, for example by involving only a single restriction enzyme treatment. These choices are well within the ability of the skilled person working the invention. In a preferred embodiment, two identical sites are introduced for removal and replacement of the loop. Preferably restriction sites used at the sequences coding for the mutational changes are different so that insertions or modifications at each of these four locations in the coding sequence can be made using a different restriction enzyme for ease of manipulation.

Position 4 Mutation

The term 'position 4 mutation' is used herein to describe mutation around, preferably close to or preferably at, the G4 site of stefin A, or W4 site of STM, mutation refers to addition(s) or insertion(s) or replacement(s) to the amino terminus amino acid residue(s) of SteA or STM. Preferably such mutations, are proximal to Pro3, preferably proximal to G4 (Stefin A) or W4 (STM). Preferably such mutations are close to, or preferably at, the Pro3 of human Stefin A or STM. Most preferred is replacement of residue 4 with R.

In a preferred embodiment, the position 4 site is used as a primary, secondary, or tertiary insertion site in addition to the other mutational changes to loop 1 and/or 2 as herein before described. The presence of R rather than G increases the accessibility of the recognition (target binding) surface since R is a positively charged amino acid and thus prevents an alpha helical loop covering the recognition site. Furthermore, the change destabilized the aptamer when alone but is stabilized once the aptamer binds to a target.

Mutation in any of Codons 46-54

The term 'mutation in any of codons 46-54' is used herein to describe mutation around, preferably close to or preferably at, the VAG site of SteA or DAG site of STM. The VAG site is residues 48-50 of the QVVAG site which is at residues 46-50 of human SteA. The DAG site is residues 48-50 of the QVDAG site which is at residues 46-50 of STM.

Preferably this refers to addition(s) or insertion(s) or replacement(s) around, preferably close to or preferably at the VAG/DAG sites. Preferably this refers to additions to or insertions into the VAG/DAG sites.

In a preferred embodiment, the 46-54 site is used as a primary, secondary or tertiary insertion site in combination with the mutational changes herein before described.

In one preferred embodiment the mutation at the VAG/DAG sites is LAS.

Experiments have shown that the modifications D48L and G50S lead to increased expression in a bacterial system.

Mutation in any of Codons 67-84

The term 'mutation in any of codons 67-84' is used herein to describe mutation around or preferably close to or preferably at the L73-L80 loop of human Stefin A or the P73-L80 loop of STM.

The term may refer to addition(s) to or insertion(s) at, or replacement at this site.

In one embodiment, the mutation may comprise replacement of the whole loop between L73 and L80 or P73 and L80 with any peptide sequence, preferably with a range of different target peptide sequences (preferably only one per stefin scaffold molecule) i.e. a library.

At a nucleic acid level, preferred mutations are those which result in a restriction site for insertion in the loop, and more preferably two restriction sites for replacement of the sequence encoding this loop. Particularly preferred are restriction sites are RsrII restriction sites.

In a preferred embodiment, loop 2 site is used as a primary, secondary or tertiary insertion site in combination with the mutational changes herein before described.

Two new scaffolds according to the present invention where mutational changes have been engineered at the NGP (SQM has L82R and T83S and SQT has E78A and L80R) each exhibit high expression in *E. coli*, which is most unexpected as it is a significant difference from the parent protein. Both SQM and SQT have a stable structure as shown by circular dichroism, which is unexpected as it is a significant difference from the parent protein.

Peptides inserted into these aptamers are available to solvents as shown by antibody binding experiments and advantageously these proteins retain their binding and function when attached to a solid surface. Furthermore, they have an increased surface area due to the positions for three inserts and therefore give higher affinity binding and experiments have shown that SQM folds correctly with a specific set of peptide inserts and does not form dimers which can mask binding sites, this is in contrast to STM and thus provides significant advantages over the prior art. Moreover with the scaffolds of the present invention peptide aptamer libraries can be made using for example SQM and thus aptamers can been identified that have the potential to interact with targets in human tissue due to the multiple binding surfaces.

Insertions

Preferably, inserts are close to or preferably at the L73-L80 loop of human Stefin A or the P73-L80 loop of STM and more preferably with two residues LeuAla encoded by the annealing sequence and thus the scaffold protein is two residues longer than the original Stefin A.

Combination Mutations

Preferably a scaffold protein according to the present invention is based on Stefin A or STM and comprises at least one of the mutations described above. Preferably the scaffold protein comprises at least two or all three of the mutations as described above. Preferably a scaffold protein according to the present invention possesses all three mutations described above, with the rest of the protein resembling either Stefin A or STM or one of the other variants. Additionally or alternatively where the terminal mutation is at position 72/73 or 82/83 it is followed by a stop codon that removes or replaces the last 25 or the last 15 amino acids of either Stefin A or STM. Target peptides may advantageously be inserted at any of the three preferred mutation sites. In the highly preferred embodiment the Stefin A/STM based scaffold proteins allow the use of three surfaces in total. These are the surfaces defined by position 4, loop 1 and loop2 (FIG. 2).

Solid Phase and Microarrays

As noted above, the invention finds application in microarrays. In solid phase embodiments such as microarray embodiments, the scaffold proteins of the invention are preferably engineered to facilitate its association or attachment to the solid phase substrate for the assay. Preferably this is by sticking to a gold coating, or by association with biotin. In order to engineer the scaffold for sticking to gold coating, preferably one or more Cys residues is introduced at the C or N terminus of the scaffold protein. In order to engineer the scaffold for immobilisation by attachment to biotin, preferably one or more copies of an eight amino acid biotin binding domain ('streptag') is introduced into said scaffold. Immobilisation may be by one or more of these or any other suitable means. Preferably the scaffold protein of the invention is immobilised. Preferably the scaffold proteins of the invention are engineered for immobilisation. Preferably interaction tests according to the present invention are carried out using immobilised scaffold proteins.

Further Advantages of the Invention

Scaffold proteins based on Stefin A are superior to using peptides because they can be used in vivo. Furthermore, employing recombinant systems they are cheaper than working with synthetic peptides. Furthermore, construction of libraries is cheaper than using synthetic libraries for the same reason, and also because they can be rationally designed using nucleic acid manipulation. This reduces the reliance on complicated chemistry for peptide synthesis.

Scaffold proteins based on Stefin A are superior to prior art such as phage display since they are internal to the cell, whereas phage display relies on extracellular interaction. Furthermore, scaffold proteins of the present invention can be used to work on native targets rather than recombinant targets. This has a further advantage of allowing examination of post translationally modified proteins which will be correctly phosphorylated or glycosylated or otherwise post-translationally modified in vivo but which would probably not be correctly formed if produced in vitro.

A further advantage of scaffold proteins according to the present invention is that they allow interrogation of the naturally occurring spectrum of splice variants and post translational modification variants which are produced in vivo without having to individually manufacture each of them and array them or otherwise compartmentalise them for analysis.

A further application of the invention is in the use of microcantilevers as a read out for interaction with Stefin A based scaffold proteins. Furthermore, the scaffold proteins of the present invention are particularly suitable for use with electrochemical and/or thin film transistor type readouts.

A yet further advantage of the scaffold of the present invention is that the peptide aptamers of the present invention can substitute for antibodies and results have shown that they may even perform better as, for example, CDK2 was detected more rapidly using peptide aptamers than antibodies. Accordingly, use of peptide aptamers rather than antibodies means that fewer animals will need to be used in the production of molecular probes which offers significant advantages to scientific research.

The present invention will now be described by way of example, in which reference will be made to the following figures.

BRIEF DESCRIPTION OF THE DRAWINGS

FIG. 1 shows expression and solubility of STM and variants in *E coli*.

FIG. 10 A shows a comparison of 33 nM solutions of Anti-Myc (red), Anti-Ha (blue) and Anti-Au1 (green) in pH 7.3, 10 mM phosphate buffer being immobilised on a chemisorbed SQM (Nt Ha, L1 Au1, L2 Myc) monolayer (black). FIG. 10B shows SPR response at variable concentration of Anti-Myc fitted to the saturation kinetics function $M=(C\times B_{max})/(C+K)$, giving rise to an equilibrium constant of $50\times10^{-9}$ M.

EXAMPLE 1

Figure 2:
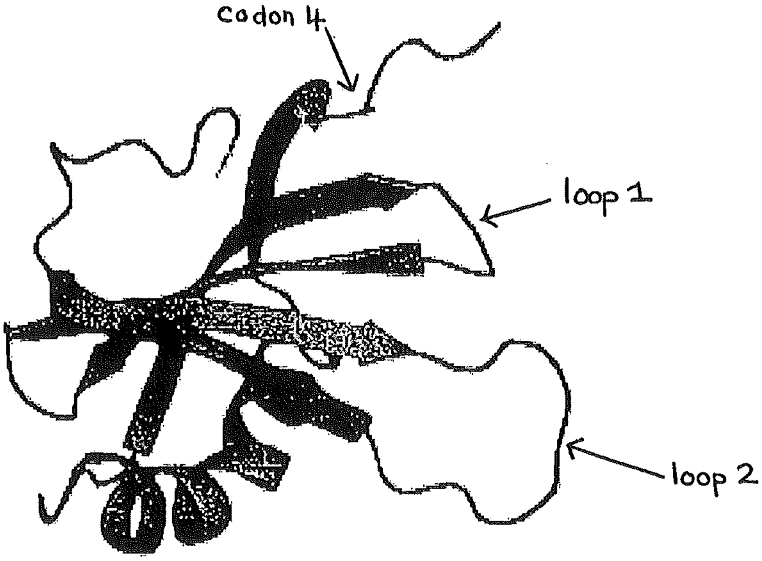
FIG. 2 shows a representation of the NMR solution structure of STM variants at codon position 4, codon positions 48-50 in loop 1, codons position 67-84 in loop 2 and codons at positions 91-92 created using Cn3D software and PDB coordinates IDVD (Martin et al. 1995 'The three-dimensional solution structure of human stefin A.' J Mol Biol, vol 246 pp 331-43). The regions that were mutated to produce the modified Stefin A proteins are indicated.

With reference to FIG. 2 there is shown a three dimensional structure of Stefin A and three sites in Stefin A which are mutated in order to generate the new scaffold proteins of the present invention. These sites are: at position G4 of Stefin A or W4 of STM; any of codons 46 to 54 inclusive of constraining loop 1 and particularly at codon positions 48-50; any of codons and; any of codons 67 to 84 inclusive of constraining loop 2 and particularly mutations of 70-73. Modified Stefin A or STM polypeptides for use as scaffold proteins are produced by mutating the sequence of Stefin A as described. The resulting proteins based on Stefin A but possessing the specified mutational changes are given in the sequences herein before disclosed.

EXAMPLE 2

Figure 1A:
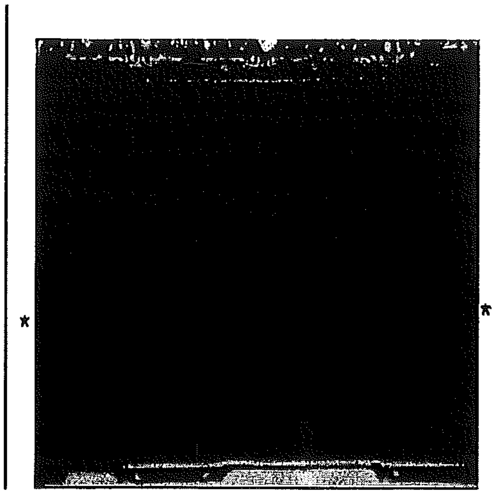
FIG. 1A shows the SUN, SUM and STM variants.
Figure 1B:
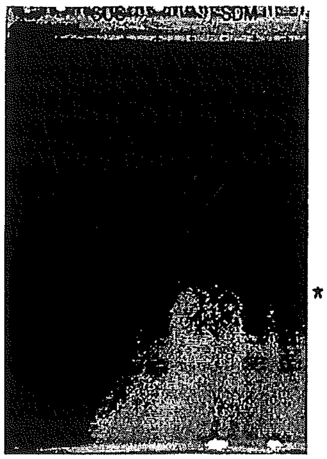
FIG. 1B shows the SUC and SDM variants and FIG. 1C shows the SQM variant.
Figure 1C:
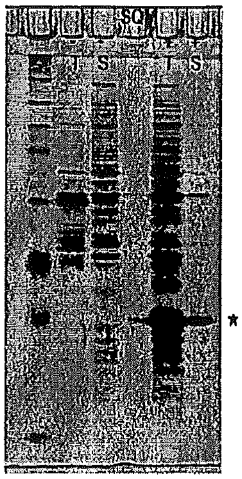

FIG. 1 shows the expression of STM and exemplar variants in *E coli*. The open reading frames for STM and the variants disclosed herein were cloned into a version of the *E coli* expression vector pET30a+ which has been engineered to include additional functionalities in the amino terminal tail, such as a cysteine residue (present in all variants shown) or a StrepII tag (in STM only). The additional 8 amino acids of the inserted StrepII tag account for the slight difference in migration of the STM protein compared to the other variants. *E coli* cells carrying these expression constructs were grown in the absence (−) or the presence (+) of isopropyl-β-d-thiogalactopyranoside (IPTG), which induces the expression of STM and the variant proteins (highlighted by *). After 3 hours of induction at 37 C, cells were lysed by sonication, and the total cell lysate (T) or the soluble (S) portion recovered after a 10 minute centrifugation at 16,000×g were loaded onto 15% polyacrylamide gels. Proteins were visualised by Coomassie staining. As far as can be determined by this method, 100% of each protein shown (SUN, SUM, STM, SUC, SDM and SQM) could be recovered in the soluble fraction, indicating that the variant proteins remain able to fold in *E coli.*

EXAMPLE 3

In the production of new scaffold proteins based on Stefin A and/or STM a rational approach to the design of a new peptide has been employed. It is desirable for the new scaffold proteins of the present invention to possess qualities that an ideal scaffold would need to possess to be broadly useful for in vitro and in vivo studies and apply these criteria to the design of a new scaffold.

Starting from the small, stable intracellular protease inhibitor Stefin A or STM, we have engineered a number of biologically neutral scaffolds that retain the stable conformation of the parent protein. We expect that modified new scaffold proteins are able to present peptides that bind to targets of interest, both in the context of known interactors and in a library screen. Molecular tools based on the scaffolds find application in a wide range of studies of biological pathways, and in the validation of drug targets. SteA is a monomeric, single domain protein of 98 amino acids that receives no known post-translational modification and lacks disulphide bonds. SteA shows remarkable thermostability with a reversible transition observed at 90.8° C. and folding enthalpy of 490 kJ/mol, all important features of a SteA-based scaffold.

EXAMPLE 4

STM variant expression plasmids (all using pET30a+) were transformed into *E coli*. Single colonies were inoculated into overnight cultures for growth at 37 C with shaking (250 rpm on an orbital shaker). The following morning, 0.5 mL of each overnight culture was inoculated into 500 mL fresh medium, supplemented with kanamycin to maintain selection for the pET30 plasmids. Variant protein expression was induced once the cultures reached mid log phase (OD600~0.6-0.8). The cultures were grown for a further 3 hours, still at 37 C with shaking. *E coli* cells were harvested by centrifugation and lysed using a French Press. The lysates were clarified by centrifugation and STM variant proteins were purified from the resulting supernatants using Ni-chelate affinity chromatography. For this, 0.5 mL of Ni-NTA agarose (QIAgen) was used per 20 mL lysate. The resin was centrifuged in 50 mL Falcon tubes at 700 g for 2 min and the supernatant was discarded. The resin was washed three times with 2.5 mL of 1× Equilibration/Wash buffer, by re-suspending the resin in buffer and then centrifuging at 700 g for 2 min at 4° C. and removing the supernatant. The lysate was combined with the washed metal affinity resin and incubated on rollers for 2 h at 4° C. An aliquot of the lysate was retained for subsequent analysis. The resin was separated from the lysate by centrifugation at 700 g for 5 min at 4° C. and removing the supernatant. A further aliquot of the lysate was retained for subsequent analysis of binding efficiency. The resin was washed six times by re-suspending the beads in 10 mL Wash Buffer (50 mM $NaH_2PO_4$, 300 mM NaCl, 20 mM Imidazole, pH 7.4), then centrifuging at 700 g for 2 min at 4° C. and removing the supernatant. The resin was incubated with 1 mL of Elution Buffer (50 mM $NaH_2PO_4$, 300 mM NaCl, 150 mM Imidazole, pH7.4) for 10 min at room temperature. The suspension was centrifuged at 700 g for 5 min and the supernatant retained. This step was repeated twice more to yield two further elution fractions. The fractions with the highest protein concentrations were retained and stored at 4 C. For circular dichroism, the samples were buffer-exchanged into 50 mM phosphate buffer pH 7.4. The samples were diluted to approximately 0.3 mg/ml on the day of analysis, and accurate protein measurements were taken using a NanoDrop spectrophotometer. Where indicated in the figures, 1 mM DTT was added immediately prior to analysis. CD spectra were collected from 200 to 260 nm using a Jasco J715 spectropolarimeter. The spectra were normalized to molar protein concentration and residual molar ellipticities were plotted so as to minimise artefacts between samples.

EXAMPLE 5

In order to ascertain whether the new scaffold proteins of the present invention based on Stefin A and STM were conformationally stable and whether the alterations made at the DNA (open reading frame) level that altered the amino acid sequence of the new Stefin A/STM variants lead to decreased stability of the protein, all variants described herein were expressed and subjected to circular dichroism to compare their secondary structure composition to that of Stefin A. Referring to FIG. 1 it can be seen that all the proteins were found to be equally well expressed in *E coli*, typically to approximately 28 mg variant protein/ml of bacterial culture. Subsequently, proteins were purified to near-homogeneity by affinity-chromatography using Ni-agarose, and diluted the purified preparations to 0.3 mg/ml immediately prior to circular dichroism analysis. As mentioned before, circular dichroism analysis involves scanning the protein across a range of near-UV wavelengths, such that the ellipticity of the light is affected by secondary structure elements (alpha-helix or beta-strands) of the protein.

Figure 3:
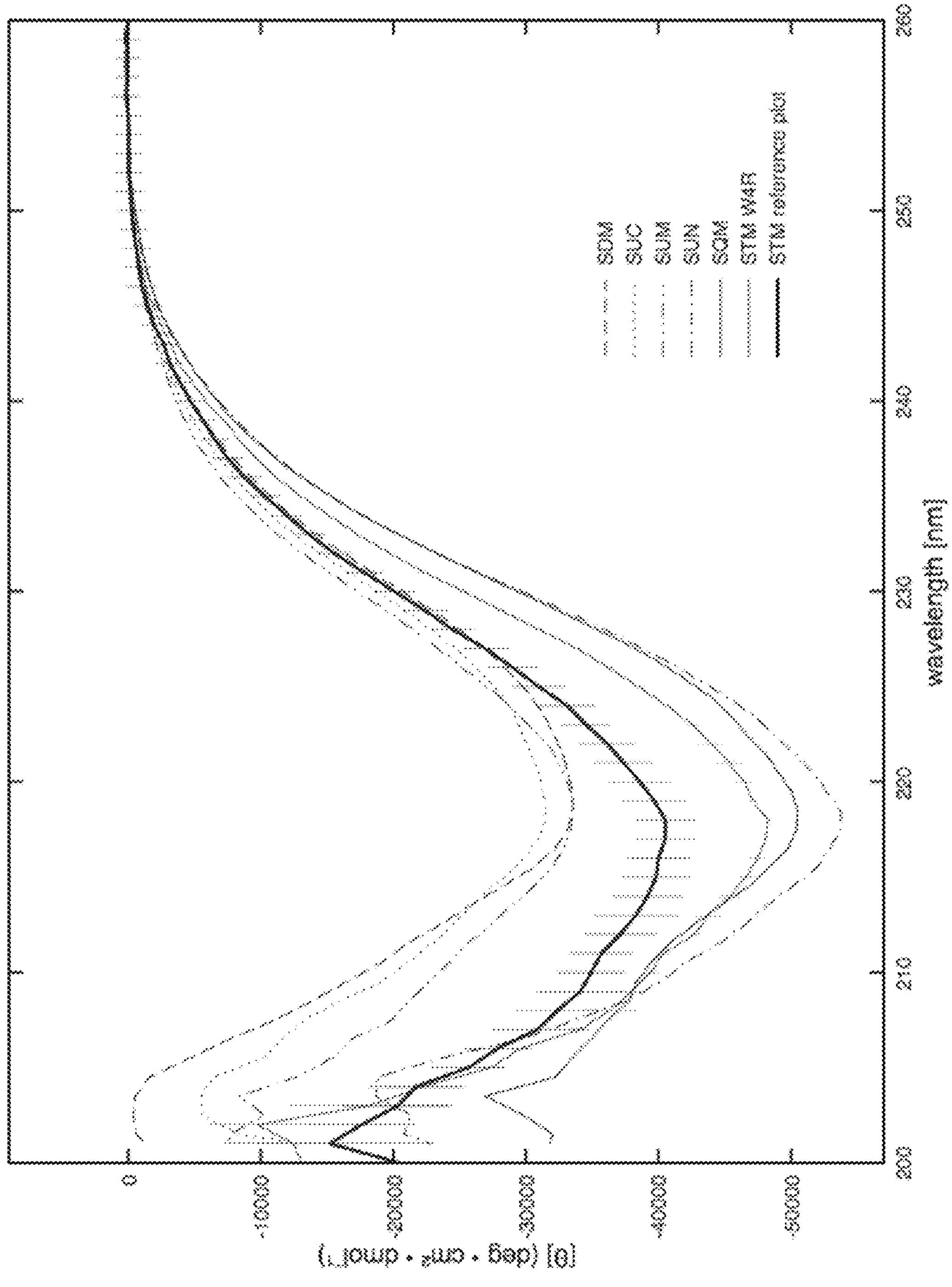
FIG. 3 shows circular dichroism (CD) spectroscopy analysis for SDM, SUC, AUM, SUN, SQM, STM W4R and a STM reference plot which measures differences in the absorption of left-handed polarized light versus right-handed polarized light which arise due to structural asymmetry so as to illustrate the proportion of secondary structure preserved between STM and the new variants.

Referring to FIG. 3 it can be seen that the proportion of secondary structure is preserved between STM and the new variants of the present invention conveniently referred to as SDM, SQM, SUM, SUN and SUC (given herein before as SEQ ID NOs: 9-13) and that the presence of inserts in STM does not adversely affect its structure. Of particular note is that two variants (SUN and SQM) appeared to show increased structure compared to other test scaffold proteins. This may be attributable to the acquisition of secondary structure in the amino terminal tail that is present in all these proteins, and would be driven by the replacement of Glycine (Stefin A) or Tryptophan (STM) at position 4 by Arginine, as this is the only change that is common to SUN and SQM, and these are the only variants to possess this alteration. When considering the minimal changes in SUN, SUM, SUC and SDM, results showed that the location of the major inflexion point at 218 nm is largely unaffected by each change (FIG. 3), indicating that, in contrast to the expectation that amino acid alterations are generally expected to destabilise proteins, the proportion of secondary structure in Stefin A derivatives is unchanged by the amino acid alterations. In contrast, the depth of the inflexion alters significantly between the variants (FIG. 3).

EXAMPLE 6

Figure 4:
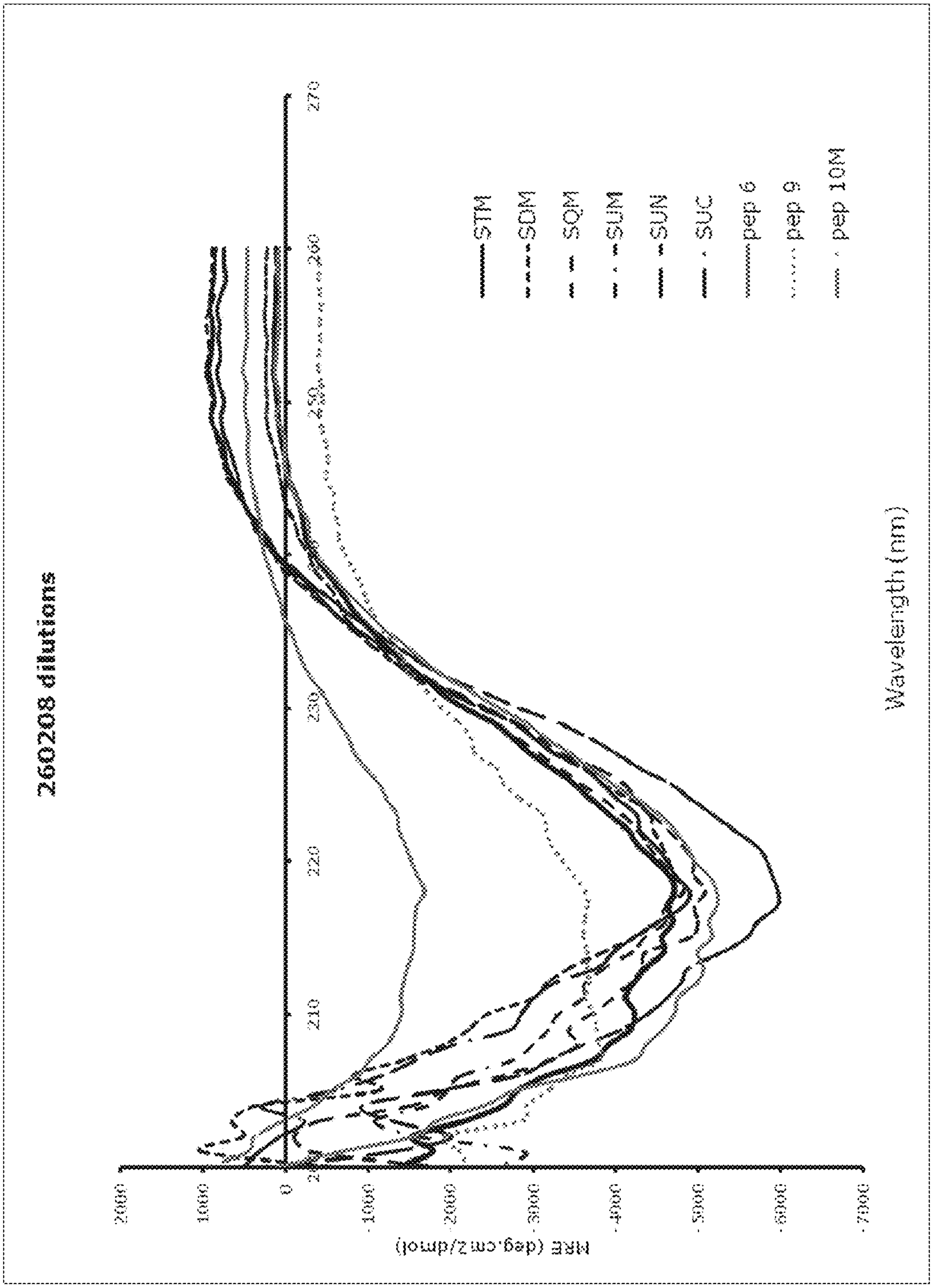
FIG. 4 shows circular dichroism (CD) spectroscopy analysis for STM, SDM, SQM, SUM, SUN, SUC, pep6M, pep9M and pep10M following prolonged storage.
Figure 5:
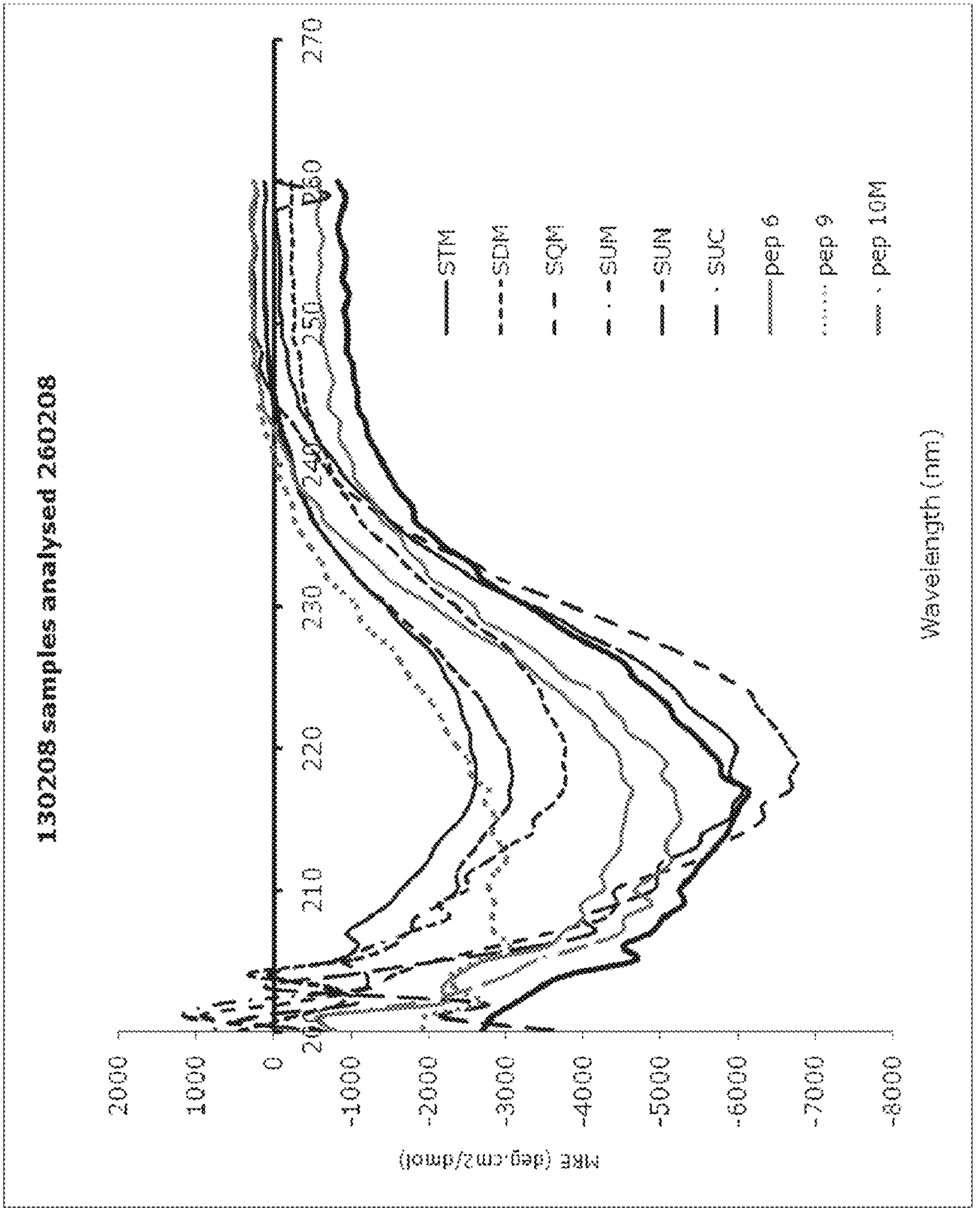
FIG. 5 shows circular dichroism (CD) spectroscopy analysis for independent preparations of STM, SDM, SQM, SUM, SUN, SUC, pep6M, pep9M and pep10M.

The effect of storage was investigated. FIG. 4 shows that, after storage at 4 C for two weeks in a phosphate buffer at pH7.4 of the concentrated stocks of all the scaffold protein variants tested, the proportion of secondary structure is retained when fresh dilutions of the same samples are analysed (comparison to FIG. 5). This is highly unexpected as most proteins are completely denatured, or have been lost due to adsorption to the storage vessel, by this time unless a large amount of carrier protein is added. This step i.e. addition of a carrier protein is undesirable, as the aim is to use highly purified preparations of peptide aptamers so as to minimize non-specific signals in diagnostic and analytical assays that would result from the presence of irrelevant proteins such as the carrier protein. In conclusion the new scaffold protein Stefin A variants may be stored in a simple phosphate buffer, with no apparent adverse effects.

This observation means that it is likely to aid in the industrial application of the new scaffold protein Stefin A variants.

EXAMPLE 7

Figure 6:
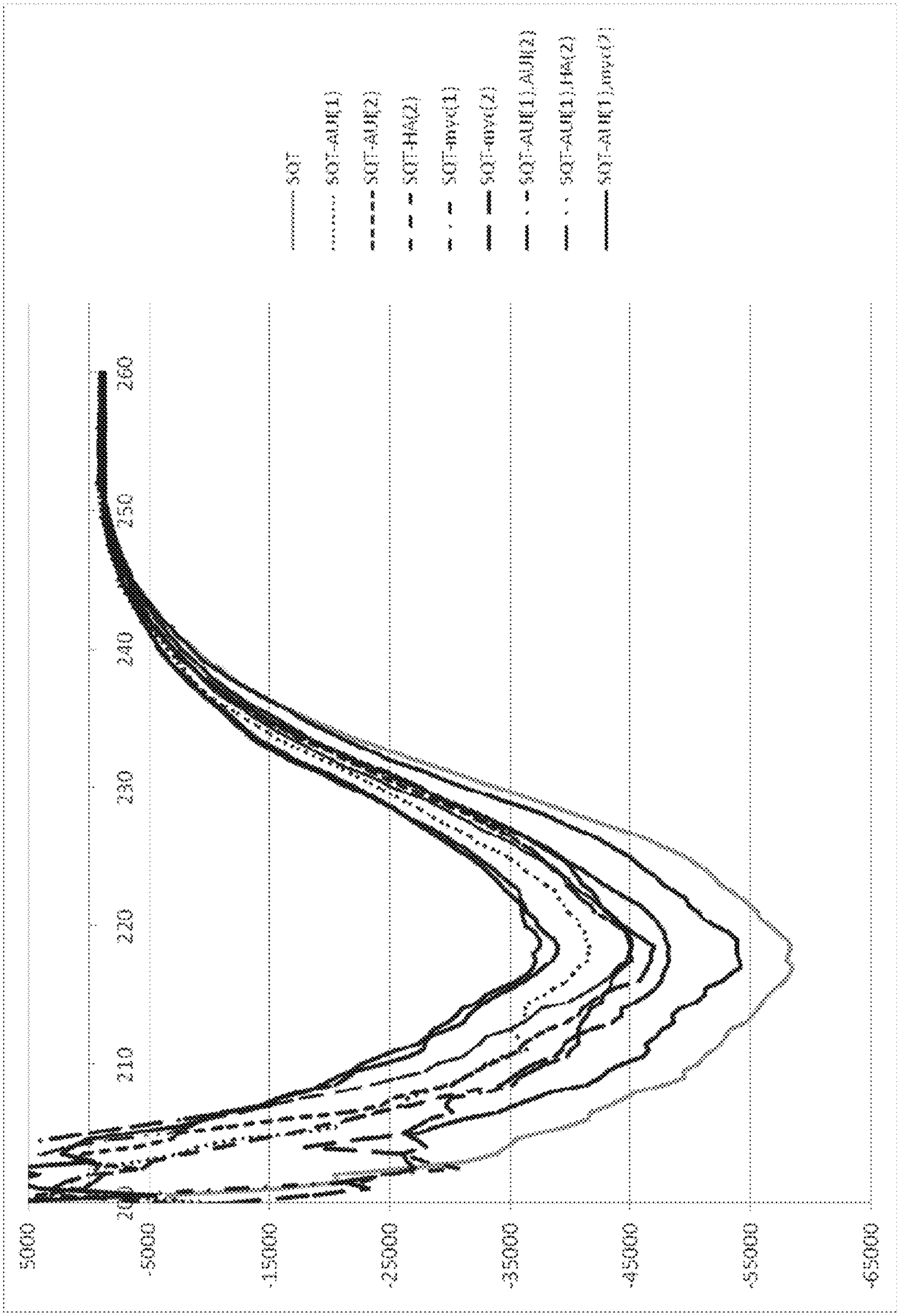
FIG. 6 shows circular dichroism (CD) spectroscopy analysis of SQT and epitope tagged variants thereof:—SQT-AUI(1), SQT-AUI(2), SQT-HA(2), SQT-myc(1), SQT-myc (2), SQT-AUI(1), AUI(2), SQT AUI(1), HA(2) and SQT-AUI(1), myc(2).

Circular dichroism was also performed on variants STM, SDM, SQM, SUM, SUN, SUC plus three peptide aptamers pep6M, pep9M and pep10M (FIG. 6). DTT was added to prevent the cysteine residues present in the amino-terminal tails of the expressed variant proteins from forming intermolecular disulphide bonds that could affect the experiment. The presence or absence of DTT did not change the observed secondary structure, although the spectra obtained in its absence were easier to interpret, as DTT itself contributes to the signal in the near-UV range. These results show that DTT does not affect secondary structure of the scaffold proteins of the present invention.

EXAMPLE 8

Figure 7:
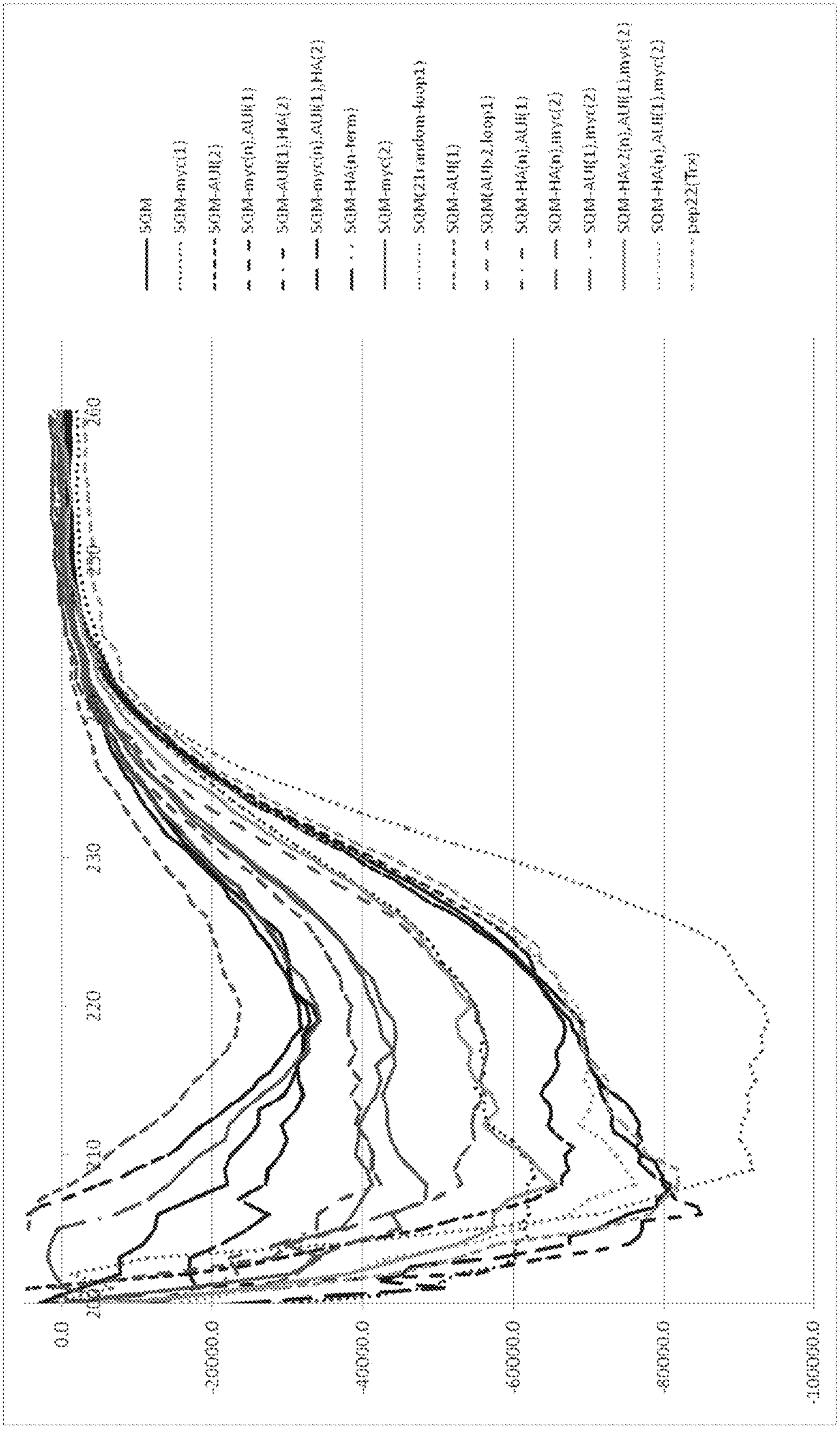
FIG. 7 shows circular dichroism (CD) spectroscopy analysis of the epitope tagged SQM variants:—SQM-myc (1), SQM-AUI(2), SQM-myc(n)AUI(1), SQM-AUI(1), HA(2), SQM-myc(n), AUI(1), HA(2), SQM-HA(n-term), SQM-myc(2), SQM(21random-loop1), SQM-AUI(1), SQM (AUIx2, loop1), SQM-HA(n), AUI(1), SQM-HA(n), myc (2), SQM-AUI(1), myc(2), SQM-HAx2(n), AUI(1), myc(2), SQM-HA(n), AUI(1), myc(2) and a peptide aptamer designated pep22(Trx).

The SQM variant (SEQ ID NO:10) which comprises a mutational change at position 4 in addition to changes in both loop 1 and 2 i.e. multiple insertion sites in a single scaffold, was assessed for its ability as a scaffold protein display system. The peptides (HA, AU1 or MYC) were inserted at positions 4, 48 and 72/82 respectively and circular dichroism data was generated (FIG. 7). The circular dichroism analysis data indicates that the new insertion sites are not only capable of presenting peptides for interaction but they do so without significant loss of structure.

EXAMPLE 9

Two methods were used to determine the effect of the amino acid changes on the scaffold structure. The first method is crudely to determine the relative expression levels of the engineered proteins in *E coli*, with the rationale that most amino acid changes are likely to destabilise the protein. Table 1 below gives the expression yields of various scaffold variants from bacterial culture, yield is given as mg purified protein per liter of culture.

TABLE 1

| SCAFFOLD | YIELD | SCAFFOLD | YIELD | INSERTION |
|---|---|---|---|---|
| STM | 59 | SQM --myc | 11 | L2 |
| SUN | 63 | SQM-AU1- | 103 | L1 |
| SUM | 48 | SQM-AUI HA | 206 | L1 + L2 |
| SUC | 71 | SQM-AU1 myc | 14 | L1 + L2 |
| SDM | 57 | SQM HA | 19 | N |
| SQM | 58 | SQM HA-myc | 4 | N + L2 |
| STM Pep2 | 19 | SQM HA AU1- | 2 | N + L1 |
| SQM Pep 2 | 9 | SQM HA AU1 myc | 2 | N + L1 + L2 |
| STM Pep6 | 36 | SQM myc AU1- | 11 | N + L1 |
| SQM Pep6 | 2 | SQM myc AU1 HA | 7 | N + L1 + L2 |
| STM Pep9 | 117, 61 | | | |
| SQM Pep9 | 21 | | | |
| STM Pep10m | 76, 40 | | | |
| SQM Pep10m | 2 | | | |
| STMA7 | 23 | | | |
| SQMA7 | 41 | | | |
| STMA48 | 52, 43 | | | |
| SQMA48 | 42 | | | |
| STMA58 | 62, 61 | | | |
| SQMA58 | 70 | | | |
| SQT | 45 | | | |

The second method used was to directly assess the proportion of secondary structure elements in each protein by circular dichroism (CD). When comparing protein yields from *E coli*, it was found that each individual change from Stefin A in SUN, SUM and SUC had little effect, or led to increased yield compared to STM (Table I). This was true also when two mutations were combined (SDM) or all three changes together in one protein, SQM. Indeed, the average yield of protein from 4 preparations of SQM was 58+/−29 mg of purified scaffold/liter bacterial culture, while the yield from three cultures of STM was 59+/−41 mg scaffold/liter of culture.

CD spectra for the different STM variants were obtained between 200 nm and 260 nm. A change in the shape of the CD spectra plot is considered to reflect changes in the α-helical and β-sheet content of the folded protein. All STM variants showed similar CD spectra with an inflexion point at about 218 nm indicating structural similarity without disrupting effects by the introduced modifications (FIG. 3). However, observed differences in the amplitude of the CD spectra were also observed with SDM, SUC, and SUM showing a flatter curve, and SQM and SUN showing a deeper curve compared to STM (FIG. 3). A possible explanation might be an enhanced stability of the folding, i.e. the averaged over-time content of correctly folded protein is higher in solutions of SQM and SUN compared to STM resulting in a higher ellipticity read out. Based on the CD spectra in combination with determined protein yields (Table 1) it is concluded that the SQM variant is likely to be a suitable scaffold protein.

EXAMPLE 10

Investigations were conducted to assess whether SQM would be able to present peptides for interaction by testing whether simple epitope tags would be able to be recognised by their cognate antibodies when presented in the new sites created in SQM. Three peptide epitopes were selected (AU1, HA and MYC tags) that differ in both length and physicochemical characteristics. These peptides were inserted singly or in various combinations into the available positions (the N terminus, loop 1 or loop2) in the scaffold. Initially, the HA tag was inserted into the amino terminal site, the AU1 tag (the shortest peptide) into loop1, and the Myc tag into loop2. Surprisingly, insertions of the HA tag into the amino terminus were only poorly tolerated, with yields of protein decreased approximately 2.5-fold compared to the empty scaffold. Similarly, Myc insertion into loop 2 resulted in >5-fold decrease in protein yield in *E coli*. In contrast, insertion of the AU1 tag into loop1 did not destabilise SQM, and may in fact increase yields (Table 1).

Taken together, the protein expression data indicate that SQM is able to present peptides from three sites—the amino terminus, loop 1 and loop2. Of these, the new loop1 site appears to be most broadly useful.

EXAMPLE 11

Experiments were conducted to assess the effects of inserting short peptides derived form existing peptide aptamers into loop 2 of the previously described STM scaffold. These peptides were of various lengths, being 10 residues (A48, A52 and A58), 17 residues (A7) and 22 residues (A52 tandem) long. Of these, only A7 affected the secondary structure of the STM protein (data not shown). Surprisingly, when the same peptides were inserted into loop 2 of SQM, the proportion of secondary structure in each resulting peptide aptamer was unchanged (data not shown). This indicates that SQM is better able to tolerate peptide insertions than STM. In addition, experiments were conducted to assess the effects of insertion of the epitope tags into the three sites as described above (Table I) on the proportion of secondary structure in the resulting peptide aptamers. Results showed unexpectedly that even those insertions that decreased protein yields did not appreciably disrupt the secondary structure of the resulting peptide aptamers (FIG. 7). However, it was noted that the presence of a peptide at the N terminal site changes the shape of the curve, pushing the inflexion point from 218 nm towards 209 nm (FIG. 7, SQM-Ha). In order to ascertain whether this may reflect a general effect of insertions at this site on the structure of the scaffold, the spectra for a range of SQM-derived peptide aptamers with inserts in loop 1 and/or loop2, all with an insert at the amino terminus was analysed. It was consistently found that these proteins possessed less secondary structure than the corresponding proteins lacking an insert at the N-terminal site (FIG. 7).

EXAMPLE 12

Figure 8A:
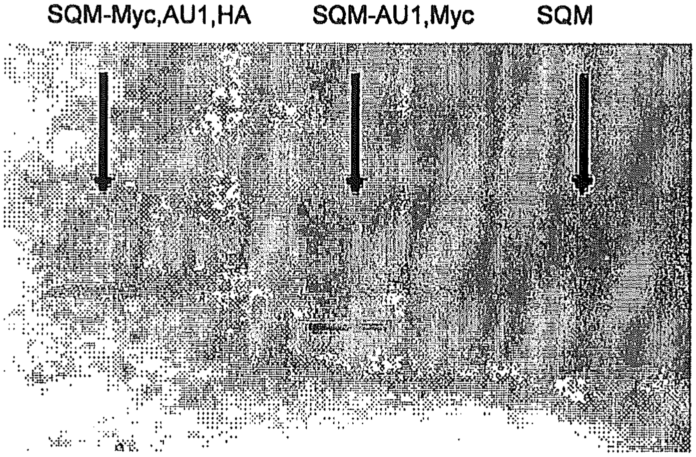
FIG. 8A shows immunoprecipitation of AUI peptide by anti-AUI antibody.
Figure 8B:
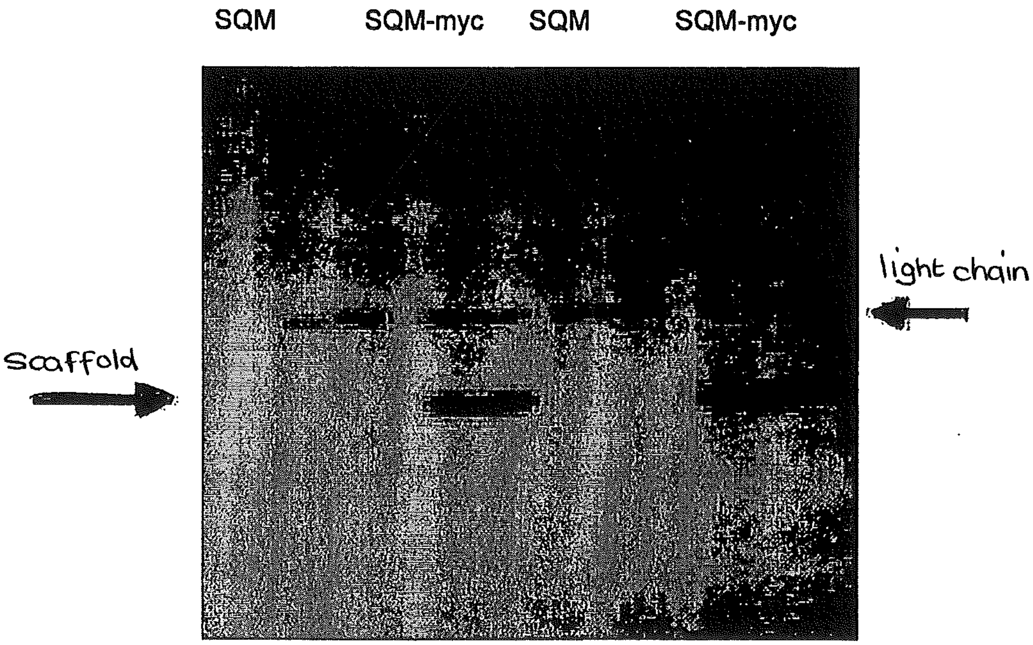
FIG. 8B shows SQM-myc (loop1) immunoprecipitation and FIG. 8C shows SQT-HA (loop2) immunoprecipitation.
Figure 8C:
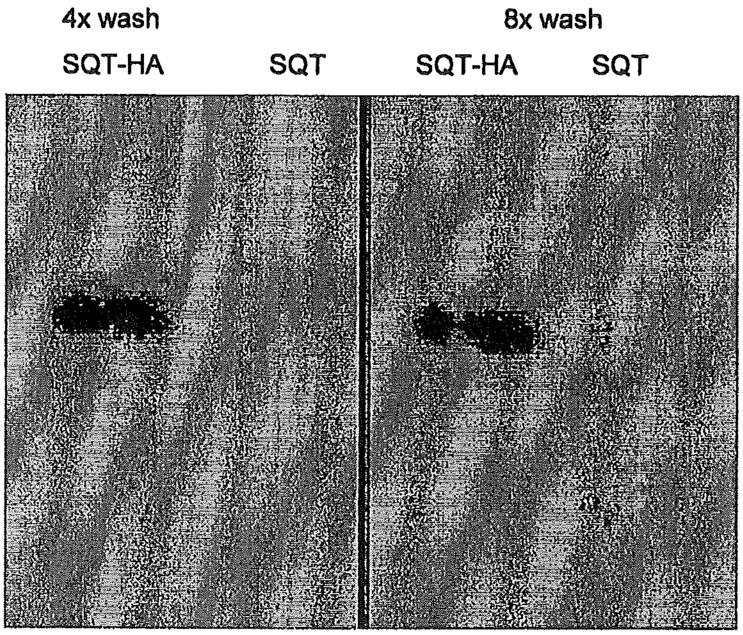
Figure 9:
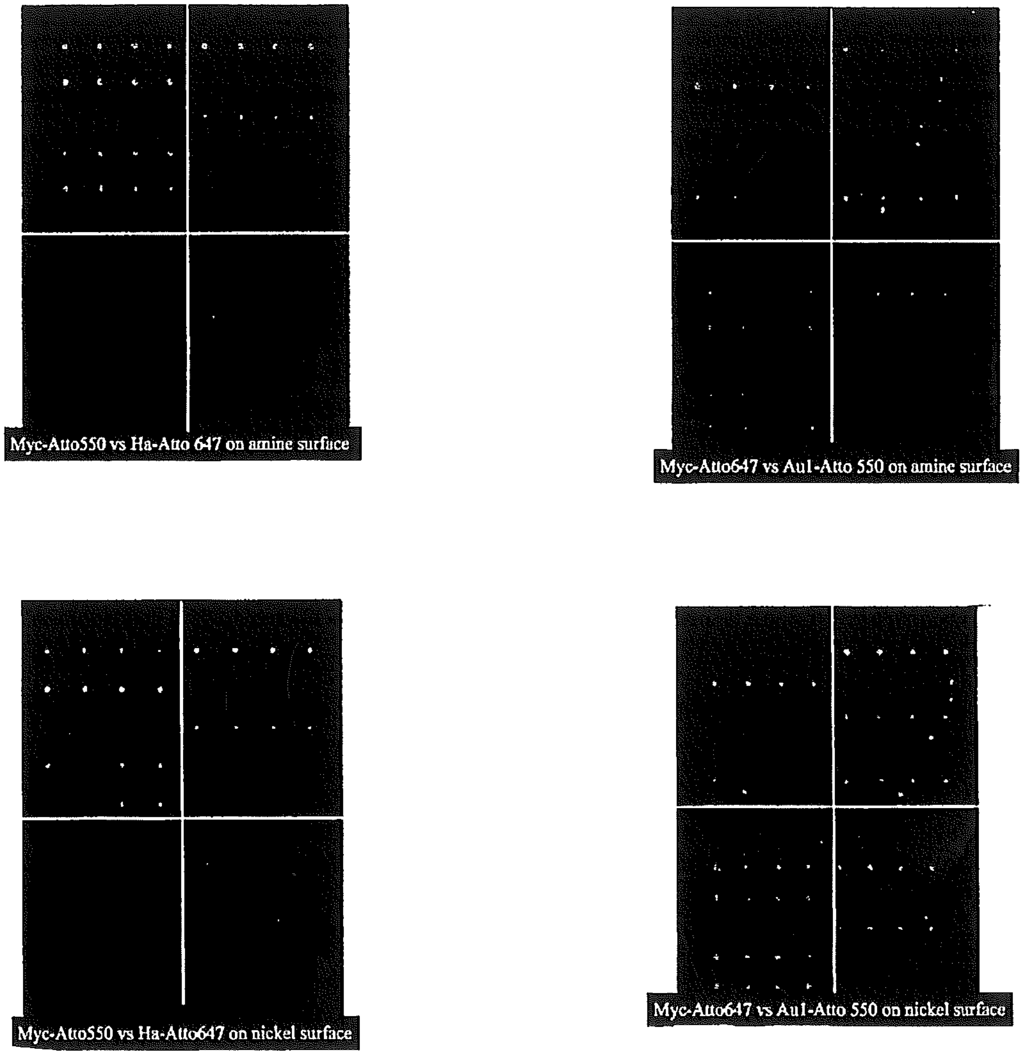
FIG. 9 shows the results of a microarray experiment with peptide aptamers with different epitopes at different positions.
Figure 10A:
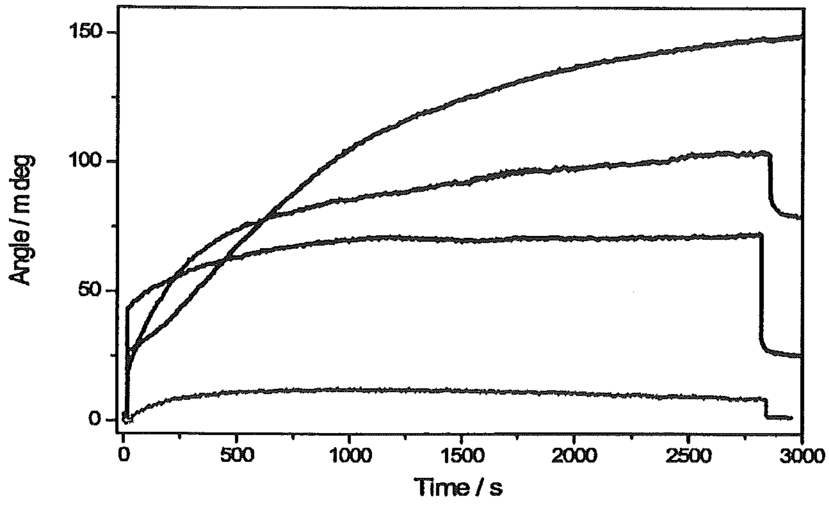
FIGS. 10A and 10B show surface plasmon resonance (SPR) measurements of antibody/epitope interactions in the context of the SQM scaffold.
Figure 10B:
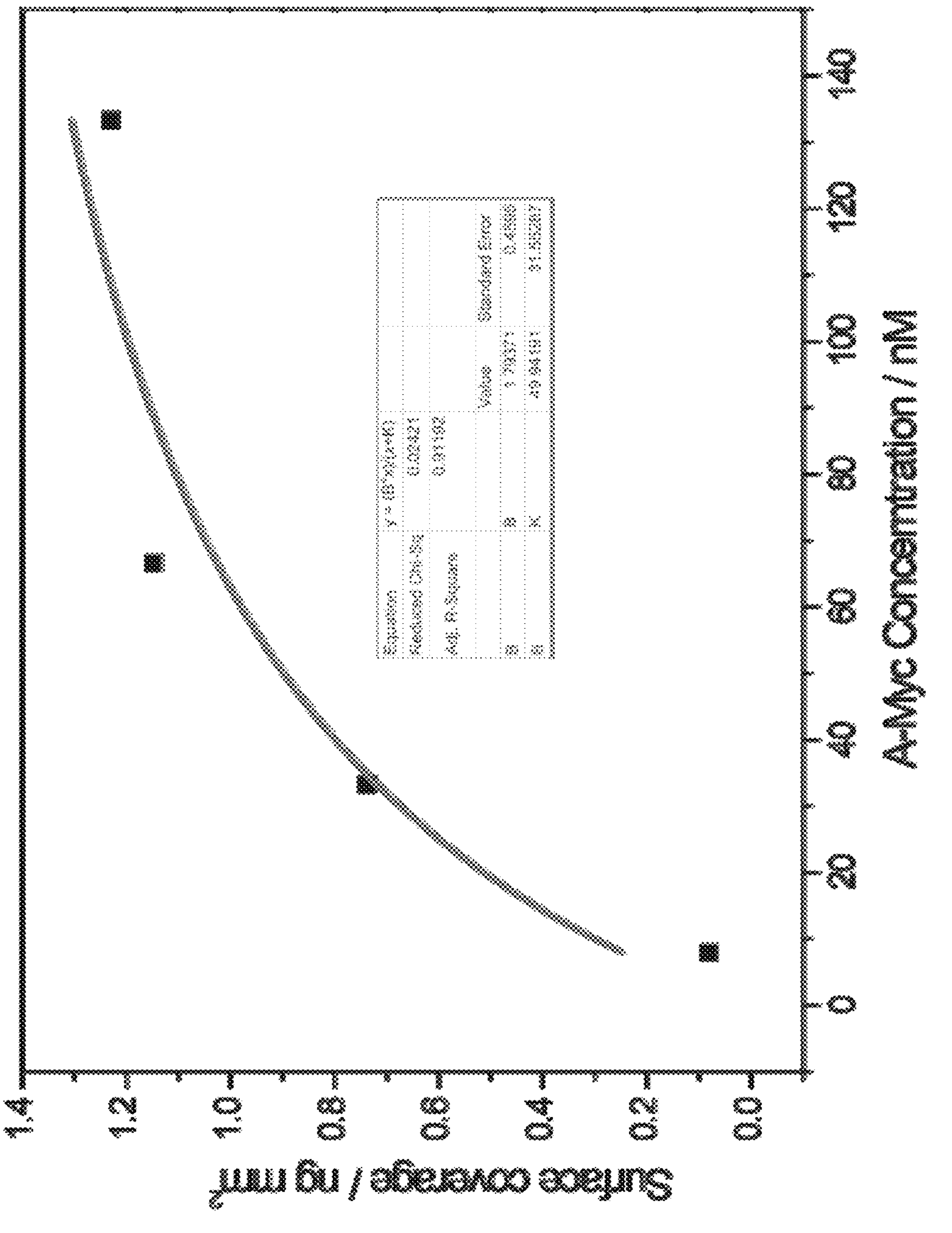

Having determined that it is possible, within limits, to insert model peptides into each of the three positions of the present invention, it was found that the inserted peptide aptamer could be immuno-precipitated. With reference to FIG. 8A, immunoprecipitation of the AU1 peptide inserted into loop 1 is shown indicating that the AU1 peptide inserted into loop 1 could be bound by an anti-AU1 antibody sufficiently tightly that the peptide aptamer could be immuno-precipitated. FIGS. 8B and 8C also show that epitopes in loop 1 of SQM (AU1 and MYC) and in loop 2 of SQT (HA) can be recognised by the cognate antibody, which can immunoprecipitate the epitope tagged scaffold variant. This was confirmed with other epitope tags being equally well recognised using a microarray format (FIG. 9). Peptide aptamers (Pep2, pep6, pep9 or pep10m) were immobilized in loop2 of SQM or SQT on a glass microscope slide using amine chemistry and probed with soluble, unlabelled; commercially sourced active CDK2 (New England Biolabs). After extensive washing, CDK2 bound to immobilised peptide aptamers was detected using an anti-CDK2 antibody and a labelled secondary antibody, which was imaged using a standard DNA microarray scanner. The data show that SQM can present pep6 better than any other scaffold, whereas SQT can present pep10m better than any scaffold variant and in clinically relevant range. The empty SQT scaffold gives a low signal which we set as the background. Peptide aptamers with different epitopes at different positions purified from *E coli* were printed onto glass slides coated with either a nickel chelate (which should capture the hexahistidine tag of each peptide aptamer so as to allow for controlled orientation or simply with poly-L-lysine. All prints started and finished with print buffer spots and free SQM spots which always gave no signal and acted as negative controls. In all cases antibody absorption was specific. These results have been confirmed with SPR (FIG. 10). The antibodies have the highest affinity for the SQM target in the following order: Anti-Myc, Anti-Ha and Anti-Au1, with changes in surface concentration of 0.4, 0.13 and 0.02 pM $cm^{-2}$ observed upon the injection of 33 nM solutions (see Table 2 below). These values indicate the relative qualitative amplitudes of the equilibrium constants K. The K value which has been calculated for the anti-Myc antibody to be in the order of ~50 nM, is in agreement with that for similar studies done with anti-cystatin. K values for Anti-Ha and Anti-Au1 have not been accurately determined due to their non-ideal behaviour in the SPR assay. Anti-Ha shows an immediate and intense association spike, followed by a secondary slower association component, with similar behaviour seen in the disassociation. Such behaviour indicates multiple processes occurring and may result from binding to multiple alternative conformations of the scaffold amino terminus, or even from impurities in the commercial sample. Alternatively it may be the result of very fast kinetic association and disassociation constants. AU1 behaves similarly to Myc with a well resolved association curve, but the absolute magnitude of immobilised antibody is seen to be drastically reduced by ca 2 orders of magnitude. In the cases of Ha and Au1 the K values are clearly less than $50\times10^{-9}$ M.

Table 2 shows relative responses of the antibodies to a covalently bound SQM aptamers containing all three epitope tags.

TABLE 2

| | SPR Response | | | K |
|---|---|---|---|---|
| | /Mdeg | /ng $mm^{-2}$ | /pmol $cm^{-2}$ | /M |
| SQM | 135 | 1.1 | 5 | |
| Myc 33 nM | 79 | 0.64 | 0.4 | $50\times10^{-9}$ |
| Ha 33 nM | 25 | 0.20 | 0.13 | $<50\times10^{-9}$ |
| Au1 33 nM | 3 | 0.03 | 0.02 | $<50\times10^{-9}$ |

Sample results are qualitatively identical between the two surfaces and no fundamental differences have been observed, though signal to noise and reproducibility is better on the amine surfaces. The similarity between surfaces indicates that in both random orientations and in controlled orientation scenarios, all three loops are open to the surroundings and are addressable. There is no evidence for identical epitopes placed in the N term, Loops 1 or 2 having variable binding affinities. Experiments were also repeated where antibodies were added simultaneously in mixtures at the concentrations stated above. Comparable results are seen in all cases, indicating the loops are well separated from each other and behave independently. No evidence of loops being blocked upon antibody binding to adjacent loops is seen. This indicates that the surfaces that we propose to use for peptide presentation can each be used independently of as well as in combination with the others, and that the engineered scaffold is able to present an unexpectedly large surface area for interaction, compatible with the binding of three antibody molecules simultaneously, which could be extrapolated to recognizing a protein or multi-protein complex of as much as 450 kDa.

EXAMPLE 13

Figure 11:
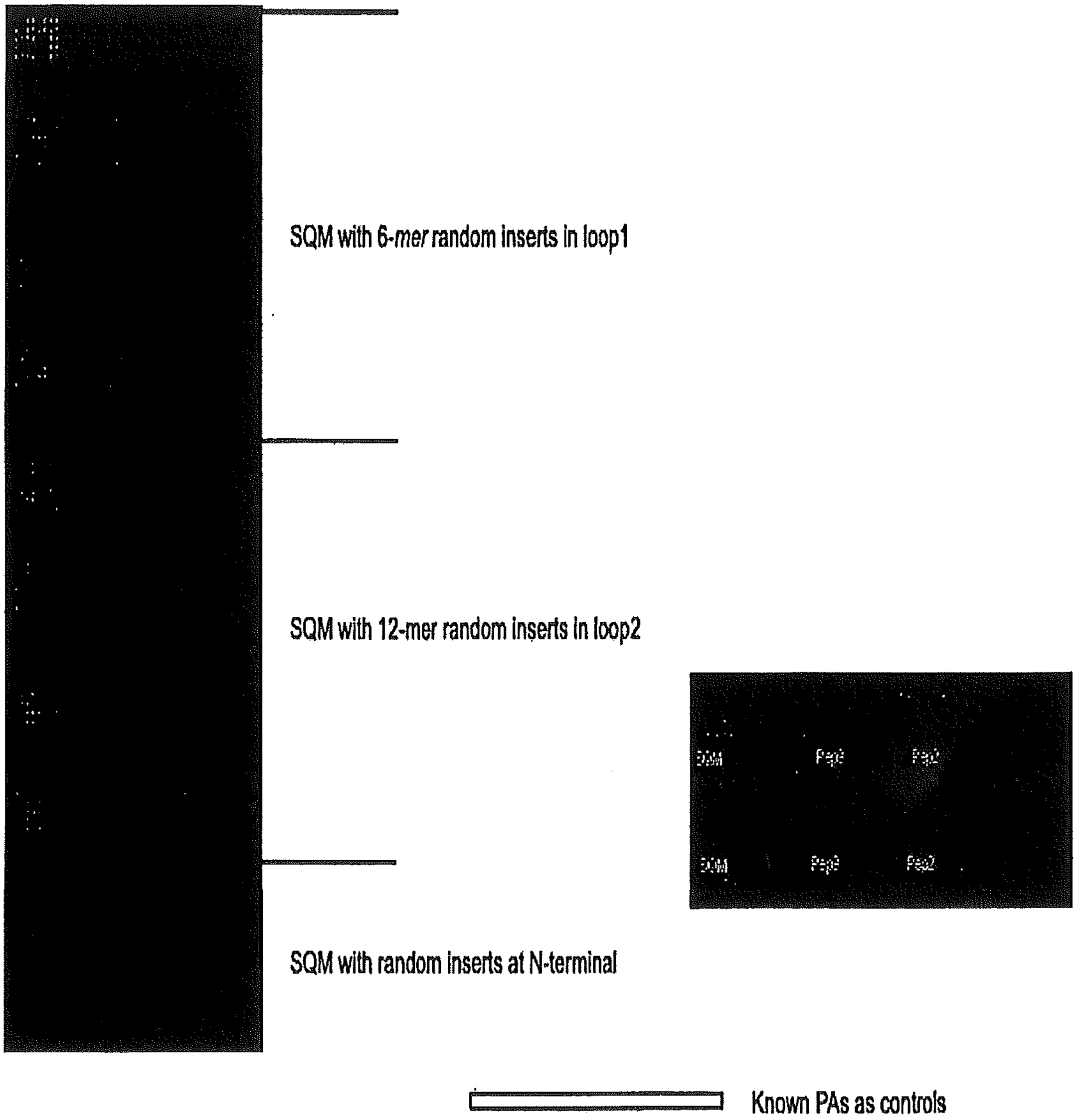
FIG. 11 the results of a microarray comprising 864 random peptide aptamers inserted into loop 1 (top) or loop 2 (centre) or the amino acid terminus (bottom).

The expression profiles of 864 random peptides inserted at each of the three sites were analysed. For this experiment, small scale cultures were grown of the random peptide aptamers in 96 well plates, purified the peptide aptamers in high throughput (i.e. without optimising expression or purification protocols for each well) and spotted an equal volume of each peptide aptamer into a glass microscope slide, creating a small microarray. The microarray was then probed with either of two antibodies that recognise the scaffold protein. The signal intensity obtained with the antibody would then be proportional to the amount of peptide aptamer at each feature of the array. Results showed that insertions at loop 1 and loop 2 were generally well expressed, while almost 50% of the amino-terminal inserts were significantly less well expressed (FIG. 11). Results showed that 68% of the 384 peptide aptamers we tested with 6 amino acid-long random inserts in loop 1 of SQM were well expressed, and 16% could be expressed to a lower level, while the expression of 15% could not be detected. 76% of the 384 peptide aptamers we tested with 12 amino acid-long random inserts in loop 2 of SQM were well expressed, while 14% could be expressed at a lower level and 10% could not be detected at all. Finally, of 192 peptide aptamers with random inserts in the amino terminus, only 35% were well expressed, while 32% were expressed at a lower level and 32% could not be detected In conclusion, although many different peptides can be presented by insertions at the amino-terminal site, these can also be frequently detrimental to the stability of the scaffold. Accordingly, it is proposed that the scaffolds and novel sites of the present invention may be used to produce peptide aptamers that interact with the target protein using a greater surface area and thus with greater affinity and specificity.

EXAMPLE 14

Further engineering of loop 2 was undertaken in an attempt to rescue the destabilising effect of the new mutation at position 82-83 compared to STM. Accordingly, a new scaffold was engineered that possesses the same changes as SQM at the amino terminus and loop 1, also has 71-NGP-73 and but now replaces the wild type (Stefin A) sequence 78-EDL-80 with either 78-ADR-80, or 77-SDRL-80, or to 78-NTD-80. Each of these changes was designed to allow us to use two RsrII sites to introduce oligonucleotides encoding peptides into loop 2. Of these, the version with 78-ADR-80 proved to be the most flexible. The new scaffold was designated as SQT (SEQ ID NO:24). It was found that protein expression yields in *E coli* for SQT were decreased compared to those for SQM (Table 3). However, the yields for versions of SQT with inserts at loop 2 were consistently improved compared to insertions of the same sequences into loop 2 of SQM (Table 3). These differences were most pronounced with AU1 in loop 2, where the expression level was less than 1 mg peptide aptamer from 1 L of bacterial culture when using SQM, but was 45 mg/L of culture with SQT. Table 3 shows the yield of peptide of peptide aptamer expresses as mg of purified protein obtained under standard conditions from 1 liter of bacterial culture.

TABLE 3

| INSERT | SQM | SQT |
|---|---|---|
| NONE | 19 | 15 |
| Pep2 | 9 | 16 |
| Pep6 | 2 | 3 |
| Pep9 | 21 | 105 |
| Pep10m | 2 | 11 |
| myc | 11 | 65 |
| AUI (loop 1) | 103 | 25 |
| AUI (loop 2) | 1 | 36 |
| AUI, AUI | nd | 49 |
| HA (loop 2) | nd | 32 |
| AUI, HA | 205 | 36 |
| myc (loop 1) | 7 | 34 |
| Myc (loop 2) | 11 | 49 |
| AUI, myc | 14 | 52 |

One surprising observation was that expression yields for inserts into loop 1 alone could be greater for SQM than for SQT. For example, 25 mg of peptide aptamers per liter of culture was obtained for SQT-AU1-loop1, but 103 mg per liter for SQM-AU1-loop 1, although this not universal, as the effect was reversed for peptide aptamers with the Myc epitope in loop 1 (Table 3). Peptide aptamers with double insertions in loop 1 and loop 2 of SQT were generally well-expressed, and showed improved yields over the same combinations in SQM, although we obtained our highest yield of a peptide aptamer to date when inserting the AU1 tag into loop 1 and the HA tag into loop 2 of SQM (Table 3).

When considering the effects of alternative peptide insertions, SQT was found to be able to present the model CDK-binding peptides (pep2, 6, 9 and 10m) or the Myc epitope. Generally, SQT was better able to accept these peptides than SQM. However, surprisingly, SQT appeared to possess little (pep2, pep9) or no (pep6, pep10m) advantage over STM. These data suggest that minimal engineering of the scaffold and peptide insertion into a loop is more readily accommodated than more complex alterations, even if these are designed to minimise disruption of the secondary structure.

EXAMPLE 15

In order to improve the efficiency of library construction using loop 1 of SQT, we inserted 5'-AGGCCTTGATCACCATGGACTAGCA-3' (SEQ ID NO:26) into the NheI site an oligonucleotide of sequence, using an NheI site at the 5' end and an SpeI site at the 3' end, the latter is lost when it anneals to the cut NheI site and this also results in the loss of the 3' NheI site in the STM open reading frame. The inserted oligonucleotide carries 3 new restriction sites (StuI, BclI and NcoI) which may be used for the insertion of peptide-encoding oligonulceotides. The final sequence of the modified scaffold in this region, including the new linker is: DNA: 5'-AAGTGCTAGCAGGCCTTGATCACCATGGAC TAGCAAGCACAAATTA-3' (SEQ ID NO:27). Protein: (N-terminus) 44-KTQVLAgldhhgla STNYYIKVRAG (C terminus), SEQ ID NO:28, with the amino acids encoded by the inserted oligonucleotide given in lower case. Note that using the NheI and NcoI sites of the linker to insert oligonucleotides will result in inserts terminating with two residues (LeuAla) encoded by the SpeI/NheI annealing sequence, and the SQT scaffold protein is thus two residues longer than the original Stefin A. We call this elongated scaffold SQL. In order to ask whether this strategy improves library construction, we inserted a random oligonucleotide flanked by 5'-NheI and 3'-NcoI sites into the corresponding sites in SQL. All 20 of the transformants that we sequenced showed correct insertion of a single oligonucleotide in each clone. in contrast, when we used the NheI site alone and cloned and sequenced 24 of the transformants, only 8 were as required (single inserts, correct orientation). Nine other clones were empty plasmid (indicating inefficient digestion and dephosphorylation steps), 3 were concatamers (where oligonucleotides ligate to each other prior to ligating into the scaffold ORF) and 4 were in the wrong orientation. These numbers show a vast improvement in using orientated insertion over those obtained when randon oligonucleotides flanked at both ends with an NheI site are inserted into the NheI sote of SQT. Accordingly, we have implemented a similar strategy with loop 2, by changing the nucleotide sequence of the open reading frame to create an XmaI site instead of the RsrII site of SQT. This does not change the amino acid sequence of SQT.

EXAMPLE 16

Figure 12:
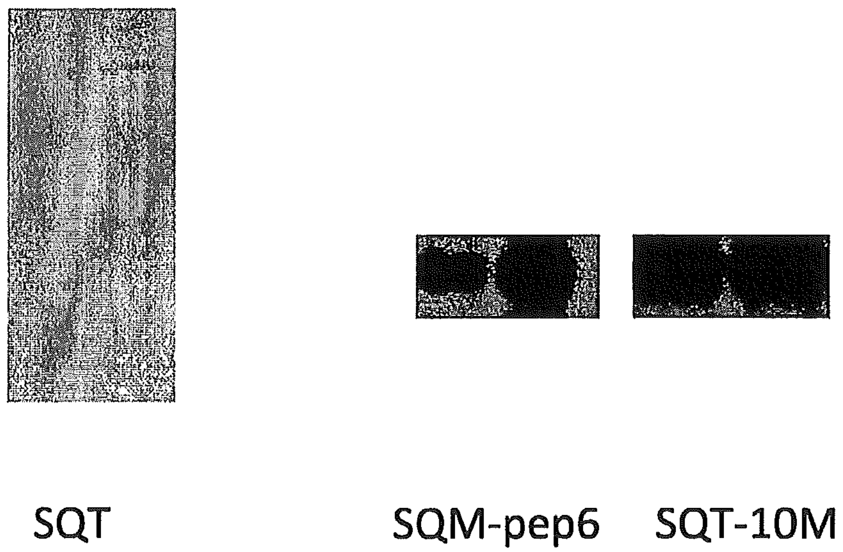
FIG. 12 shows the use of peptide aptamers in SQM (SQM-pep6) and SQT (SQT-pep10m) to detect endogenous cdk2 expression in duplicate lysates of human (HeLa) cells.

The two peptide aptamers showing the highest apparent affinity for CDK2 from the microarray experiment were used in an "immuno-blotting" protocol (also called a western blot see FIG. 12), except that the peptide aptamers (SQM-pep6 and SQT-pep10M) were used instead of antibodies. Antibodies were similarly omitted from the development step of the "immuno-blot" as the peptide aptamers possess an S-tag which can be detected using S-protein fused to horse radish peroxidase (HRP). As a negative control, parallel blots were probed with the empty scaffold (SQT is shown) and developed using the S protein protocol. As a positive control, parallel blots were probed with an anti-cdk2 antibody, which was able to detect a protein of the same relative molecular weight, although longer exposure times were required when the antibody was used at the same concentration as the peptide aptamers. FIG. 12 shows two lysates of human tissue culture cells that were subject to denaturing polyacrylamide gel electrophoresis prior to being transferred to nitrocellulose or PVDF membranes and probed with scaffold, peptide aptamers or scaffold as described above. The data show that peptide aptamers can not only substitute for antibodies in this protocol, but actually perform better as CDK2 was detected more rapidly using peptide aptamers than antibodies. Thus advantageously, use of peptide aptamers rather than antibodies means that fewer animals will need to be used in the production of molecular probes.

The invention claimed is:

1. A Stefin A polypeptide comprising an amino acid sequence having at least 80% identity to the polypeptide sequence of SEQ ID NO: 1; said polypeptide comprising a mutation at position 4 wherein the Glycine of said Stefin A polypeptide is replaced by Arginine and a heterologous peptide is inserted into the polypeptide at a) the G4 site of Stefin A; or b) position 46-54; or c) position 67-84; or d) position 82/83; and an inflection at 218 nanometers as shown by circular dichroism analysis.

2. The Stefin A polypeptide according to claim 1, comprising a further heterologous peptide insertion, wherein at least one heterologous peptide is inserted into the protein at at least two positions selected from (a), (b), (c) and (d).

3. The Stefin A polypeptide according to claim 2, comprising a further heterologous peptide insertion, wherein at least one heterologous peptide is inserted into the protein at at least three positions selected from (a), (b), (c) and (d).

4. A Stefin A polypeptide according to claim 3 comprising a further heterologous peptide insertion, wherein at least one heterologous peptide is inserted into the protein at all four positions (a), (b), (c) and (d).

5. A polypeptide according claim 1, wherein said heterologous peptide of (a) is inserted proximal to the G4 site of Stefin A.

6. A polypeptide according claim 2, wherein said heterologous peptide of (a) is inserted proximal to the G4 site of Stefin A.

7. A polypeptide according claim 3, wherein said heterologous peptide of (a) is inserted proximal to the G4 site of Stefin A.

8. A polypeptide according claim 4, wherein said heterologous peptide of (a) is inserted proximal to the G4 site of Stefin A.

9. A Stefin A polypeptide comprising amino acid sequence having at least 80% identity to the polypeptide sequence of SEQ ID NO: 1; said polypeptide comprising a mutation at position 4 wherein the Glycine of Stefin A is replaced by Arginine and a heterologous peptide is inserted into the polypeptide at i) position 46-54; or ii) position 67-84; or iii) position 82/83; and an inflection at 218 nanometers as shown by circular dichroism analysis.

10. The Stefin A polypeptide according to claim 9, comprising a further heterologous peptide insertion, wherein at least one heterologous peptide is inserted into the protein at at least two positions selected from (i), (ii), and (iii).

11. The Stefin A polypeptide according to claim 10 comprising a further heterologous peptide insertion, wherein at least one heterologous peptide is inserted into the protein at all three positions (i), (ii), and (iii).

12. A Stefin A scaffold protein comprising the polypeptide of claim 1.

13. A microarray comprising the polypeptide of claim 1.

14. The microarray of claim 13, wherein the polypeptide is immobilized.

* * * * *